(12) United States Patent
Sinderby et al.

(10) Patent No.: US 8,256,419 B2
(45) Date of Patent: Sep. 4, 2012

(54) METHOD AND DEVICE USING MYOELECTRICAL ACTIVITY FOR OPTIMIZING A PATIENT'S VENTILATORY ASSIST

(75) Inventors: Christer Sinderby, Toronto (CA); Jennifer Beck, Toronto (CA); Jadranka Spahija, Mount Royal (CA); Lars Lindstrom, Mölndal (SE)

(73) Assignee: Maquet Critical Care AB, Solna (SE)

( * ) Notice: Subject to any disclaimer, the term of this patent is extended or adjusted under 35 U.S.C. 154(b) by 1187 days.

(21) Appl. No.: 10/589,385

(22) PCT Filed: Feb. 18, 2005

(86) PCT No.: PCT/CA2005/000217
§ 371 (c)(1),
(2), (4) Date: Aug. 22, 2007

(87) PCT Pub. No.: WO2005/077268
PCT Pub. Date: Aug. 25, 2005

(65) Prior Publication Data
US 2008/0121231 A1 May 29, 2008

Related U.S. Application Data

(60) Provisional application No. 60/545,577, filed on Feb. 18, 2004.

(51) Int. Cl.
*A61M 11/00* (2006.01)
(52) U.S. Cl. .............................. 128/204.23; 128/204.21

(58) Field of Classification Search .............. 128/200.24, 128/204.18, 204.21, 204.23, 204.26, 205.23, 128/207.14; 600/529
See application file for complete search history.

(56) References Cited

U.S. PATENT DOCUMENTS

| 5,671,752 | A | 9/1997 | Sinderby et al. ............... 600/546 |
| 6,584,973 | B1 | 7/2003 | Biondi et al. .............. 128/204.21 |
| 7,425,201 | B2 * | 9/2008 | Euliano et al. ................ 600/529 |
| 2003/0079750 | A1 | 5/2003 | Berthon-Jones .......... 128/204.18 |
| 2003/0188748 | A1 | 10/2003 | Sinderby et al. .......... 128/204.21 |

FOREIGN PATENT DOCUMENTS

| EP | 1366779 | 12/2003 |
| WO | WO 02/056818 | 7/2002 |

OTHER PUBLICATIONS

Aldrich et al., "Electrophysiologic techniques for the assessment of respiratory muscle function," In: ATS/ERS Statement on respiratory muscle testing, *Am. J. Respir. Crit. Care Med.*, 166:548-558, 2002.

(Continued)

*Primary Examiner* — Steven Douglas
(74) *Attorney, Agent, or Firm* — Fulbright & Jaworski LLP

(57) ABSTRACT

The present invention relates to a method and device for determining a level of ventilatory assist to a ventilator-dependent patient, in which a critical threshold of a respiration-related feature is calculated. Fatigue of a respiratory muscle of the ventilator-dependent patient develops when the critical threshold is reached by the respiration-related feature. The level of ventilatory assist to the ventilator-dependent patient is controlled in relation to the critical threshold of the respiration-related feature so as to prevent fatigue of the patient's respiratory muscle.

18 Claims, 7 Drawing Sheets

OTHER PUBLICATIONS

Beck et al., "Diaphragm interference pattern EMG and compound muscle action potentials: effects of chest wall configuration," *J. Appl. Physiol.*, 82:520-530, 1997.

Beck et al., "Effects of lung volume on diaphragm EMG signal strength during voluntary contractions," *J. Appl. Physiol.*, 85:1123-1134, 1998.

Beck et al., "Effects of muscle-to-electrode distance on the human diaphragm electromyogram," *J. Appl. Physiol.*, 79:975-985, 1995.

Beck et al., "Influence of bipolar esophageal electrode positioning on measurements of human crural diaphragm electromyogram," *J. Appl. Physiol.*, 81:1434-1449, 1996.

Bellemare and Grassino, "Effect of pressure and timing of contraction on human diaphragm failure," *J. Appl. Physiol: Respirat. Environ. Exercise Physiol.*, 53:1190-1195, 1982.

Bellemare and Grassino, "Evaluation of human diaphragm fatigue," *J. Appl. Physiol: Respirat. Environ. Exercise Physiol.*, 53:1196-1206, 1982.

Brochard et al., "Inspiratory pressure support prevents diaphragmatic fatigue during weaning from mechanical ventilation," *Am. Rev. Respir. Dis.*, 139:513-521, 1989.

Broman, "An investigation on the influence of a sustained contraction on the succession of action potentials from a single motor unit," *Electromyogr. Clin. Neurophysiol.*, 17:341-358, 1977.

Calzia et al., "Pressure-time product and work of breathing during biphasic continuous positive airway pressure and assisted spontaneous breathing," *Am. J. Respir. Crit. Care Med.*, 150:904-910, 1994.

Clanton et al., "Preservation of sustainable inspiratory muscle pressure at increased end-expiratory lung volume," *Am. Rev. Respir. Dis.*, 147:385-391, 1993.

Clausen et al., "$K^+$ induced inhibition of contractile force in rat skeletal muscle, role of active $Na^+$-$K^+$ transport," *Am. J. Physiol.*, 261:C799-C807, 1991.

Cohen et al., "Clinical manifestations of inspiratory muscle fatigue," *Am. J. Med.*, 73:308-316, 1982.

Farkas and Roussos, "Acute diaphragmatic shortening: in vitro mechanics and fatigue," *Am. Rev. Respir. Dis.*, 130:434-438, 1984.

Gandevia and McKenzie, "Human diaphragmatic EMG: changes with lung volume and posture during supramaximal phrenic stimulation," *J. Appl. Physiol.*, 60:1420-1428, 1986.

Gross et al., "Electromyogram pattern of diaphragmatic fatigue," *J. Appl. Physiol.: Respirat. Environ. Exercise Physiol.*, 46:1-7, 1979.

Hodgkin and Huxley, "A quantitative description of membrane current and its application to conduction and excitation in nerve," *J. Physiol. (Lond)*, 117:500-544, 1952.

Hodgkin, "A note on conduction velocity," *J. Physiol (Lond)*, 125:221-224, 1954.

Hussain, "Regulation of ventilatory muscle blood flow," *J. Appl. Physiol.*, 81:1455-1468, 1996.

Jubran et al., "Variability of patient-ventilator interaction with pressure support ventilation in patients with chronic obstructive pulmonary disease," *Am. J. Respir. Crit. Care Med.*, 152:129-136, 1995.

Kadefors et al., "Dynamic spectrum analysis of myo-potentials with special reference to muscle fatigue," *Electromyog. Clin. Neurophysiol.*, 8:39-74, 1968.

Klawitter and Clanton, "Tension-time index, fatigue, and energetics in isolated rat diaphragm: a new experimental model," *J. Appl. Physiol.*, 96:89-95, 2003.

Körner et al., "The relation between spectral changes of the myoelectric signal and the intramuscular pressure of human skeletal muscle," *Eur. J. Appl. Physiol.*, 52:202-206, 1984.

Laghi et al., "Is weaning failure caused by low-frequency fatigue of the diaphragm," *Am. J. Respir. Crit. Care Med.*, 167:120-127, 2003.

Lindinger and Sjøgaard, "Potassium regulation during exercise and recovery," *Sports Med.*, 11:382-401, 1991.

Lindström and Hellsing, "Masseter muscle fatigue in man objectively quantified by analysis of myoelectric signals," *Arch. Oral Biol.*, 28:297-301, 1983.

Lindström and Magnusson, "Interpretation of myoelectric power spectra: a model and its applications," *Proc. IEEE*, 65:653-662, 1977.

Lindström and Petersén, "Power spectrum analysis of EMG signals and its applications," In: Progress in Clinical Neurophysiology. Computer-Aided Electromyography, *Prog. Clin. Neurophsyiol.*, 10:1-51, 1983.

Lindström et al., "An electromyographic index for localized muscle fatigue," *J. Appl. Physiol: Respirat. Environ. Exercise Physiol.*, 43:750-754, 1977.

Lindström, "Fatigue changes in the myoelectric signal during periodic muscle work," *Bull. Eur. Physiopathol. Respir.*, 15Suppl:107-114, 1979.

Mortimer et al., "Conduction velocity in ischemic muscle: effect on EMG frequency spectrum," *Am. J. Physiol.*, 219:1324-1329, 1970.

Ranieri et al., "Patient-ventilator interaction during acute hypercapnia: pressure-support vs. proportional-assist ventilation," *J. Appl. Physiol.*, 81:426-436, 1996.

Roussos and Macklem, "Diaphragmatic fatigue in man," *J. Appl. Physiol.: Respirat. Environ. Exercise Physiol.*, 43:189-197, 1977.

Roussos et al., "Fatigue of inspiratory muscles and their synergic behavior," *J. Appl. Physiol.: Respirat. Environ. Exercise Physiol.*, 46:897-905, 1979.

Sasson et al., "Pressure-time product during continuous positive airway pressure, pressure support ventilation, and T-piece during weaning from mechanical ventilation," *Am. Rv. Respir. Dis.*, 143:469-475, 1991.

Sinderby et al., "Automatic assessment of electromyogram quality," *J. Appl. Physiol.*, 79:1803-1815, 1995.

Sinderby et al., "Changes in respiratory effort sensation over time are linked to the frequency content of diaphragm electrical activity," *Am. J. Respir. Crit. Care Med.*, 163:905-910, 2001.

Sinderby et al., "Effects of diaphragm shortening on the mean action potential conduction velocity in canines," *J. Physiol.*, 490:207-214, 1996.

Sinderby et al., "Enhancement of signal quality in esophageal recordings of diaphragm EMG," *J. Appl. Physiol.*, 82:1370-1377, 1997.

Sinderby et al., "Influence of the bipolar electrode transfer function on the electromyogram power spectrum," *Muscle & Nerve*, 19:290-301, 1996.

Sinderby et al., "Neural control of mechanical ventilation in respiratory failure," *Nat. Med.*, 5:1433-1436, 1999.

Sinderby et al., "Voluntary activation of the human diaphragm in health and disease," *J. Appl. Physiol.*, 85:2146-2158, 1998.

Tobin et al., "Assessment of respiratory muscle function in the intensive care unit," In: ATS/ERS Statement on Respiratory Muscle Testing, *Am. J. Respir. Crit. Care Med.*; , 166:610-623, 2002.

Tobin et al., "The pattern of breathing during successful and unsuccessful trials of weaning from mechanical ventilation," *Am. Rev. Respir. Dis.*, 134:1111-1118, 1986.

Tzelepis et al., "Increased lung volume limits endurance of inspiratory muscles," *J. Appl. Physiol.*, 64:1796-1802, 1988.

PCT International Search Report, Jul. 4, 2005.

Beck et al., "Crural diaphragm activation during dynamic contractions at various inspiratory flow rates," *Journal of Applied Physiology*, 85:451-458, 1998.

Beck et al., "Electrical activity of the diaphragm during pressure support ventilation in acute respiratory failure," 1st revised version re-submitted. *Am. J. Respir. Crit. Care Med.*, 164:419-424, 2001.

Brochard, "Pressure support ventilation," In: *Principles and Practice of Mechanical Ventilation*. Ed. M. J. Tobin. Chapter 9. pp. 239-257. McGraw Hill, Inc.: New York. 1994.

Kimura et al., "Determination of the optimal pressure support level evaluated by measuring transdiaphragmatic pressure," *Chest*, 100:112-117, 1991.

MacIntyre, "Respiratory function during pressure support ventilation," *Chest*, 89(5):677-683, 1986.

Sinderby et al., "Chest wall muscle cross talk in canine costal diaphragm electromyogram," *Journal of Applied Physiology*, 81:2312-2327, 1996.

Sinderby et al., "Diaphragm activation during exercise in chronic obstructive pulmonary disease," *Am. J. Respir. Crit. Care Med.*, 163:1637-1641, 2001.

Slutsky, "Mechanical ventilation," ACCP Consensus Conference. *Chest*, 104(6):1833-59, 1993.

Yang and Tobin, "A prospective study of indexes predicting the outcome of trials of weaning from mechanical ventilation," *The New England Journal of Medicine*, 324(21):1445-1450, 1991.

American Thoracic Society Statement, "Standards for the diagnosis and care of patients with chronic obstructive pulmonary disease," *Am. J. Respir. Crit. Care Med.*, 152:S77-S120, 1995.

Appendini et al., "Partitioning of inspiratory muscle work load and pressure assistance in ventilator-dependent COPD patients," *Am. J. Crit. Care Med.*, 154:1301-1309, 1996.

Beck et al., "Reproducibility of diaphragm EMG center frequency in healthy subjects breathing against progressive inspiratory loads," *Am. J. Resp. Grit. Care Med.*, 153:A786, 1996.

Clausen, "Regulation of active Na/K transport in skeletal muscle," *Physiological Rev.*, 66:542580, 1996.

Clausen, "The NA/K pump in skeletal muscle: quantification, regulation, and functional significance," *Acta. Physiol. Scand.*, 156:227-235, 1996.

Field, "Respiratory muscle oxygen consumption estimated by the diaphragm pressure time index," *J. Appl. Physiol.*, 57:44-51, 1984.

Goldstone et al., "Weaning from mechanical ventilation," *Thorax*, 46:56-62, 1991.

Hilbert et al., "Optimal pressure support level for beginning weaning in patients with COPD: Measurement of diaphragmatic activity with step by step decreasing pressure support level," *J. Crit. Care.*, 13:110-118, 1998.

Kimura et al., "Determination of the optimal pressure support level evalulated by measuring transdiaphragmatic pressure," *Chest*, 100:112-117, 1991.

Laporta, "Assessment of transdiaphragmatic pressure in humans," *J. Appl. Physiol.*, 58:1469-1476, 1985.

Lessard et al., "Weaning from ventilator support," *Clin. Chest Med.*, 17:475-489, 1996.

Marini et al., "Estimation of inspiratory muscle strength in mechanically ventilated patients: the measurement of maximal inspiratory pressure," *Crit. Care*, 1:32-38, 1986.

Milic-Emili, "Is weaning an art or a science," Editorial, *am. Rev. Res. Dis.*, 134:1107-1108, 1986.

Multz et al., "Maximal inspiratory pressure is not a reliable test of inspiratory muscle strength in mechanically ventilated patients," *Am. Rev. Res. Dis.*, 142:529-532, 1990.

Nielsen et al., "The significance of Na/K transport in the maintenance of contractility in rat skeletal muscle," *Acta Physio. Scand.*, 157:199-209, 1996.

Rossi et al., "Respiratory mechanics in mechanically ventilated patients with respiratory failure," *J. Appl. Phyisol.*, 58:1849-1858, 1985.

Sackner et al., "Calibration of respiratory inductive plethysmography during natural breathing," *J. Appl. Physiol.*, 66:410-420, 1989.

Schulze et al., "Effects of ventilator resistance and compliance on phrenic nerve activity in spontaneously breathing cats," *Am. J. Resp. Crit. Care Med.*, 153:671-676, 1996.

Sinderby et al., "Feasibility of using diaphragm electrical activity to trigger mechanical ventilation," *European Respiratory Society Annual Meeting*, Madrid, Oct. 1999.

Sinderby et al., "Neurally adjusted proportional pressure assist," *Am. J. Resp. Crit. Care Med.*, 157:A685 1998.

Sinderby et al., "Triggering mechanical ventilation using diaphragm electrical activity in acute respiratory failure," *European Society of Intensive Care Medicine Annual Meeting*, Berlin , Oct. 1999.

Sorli et al., "Control of breathing in patients with chronic obstructive lung disease," *Clin. Sci. Mol. Med.*, 54:295-304, 1978.

Supinski, "Effect of diaphragmatic contraction on intramuscular pressure and vascular impedance," *J. Appl. Physiol.*, 68:1486-1493, 1990.

Younes, "Proportional assist ventilation, a new approach to ventilator support," *Am. Rev. Res. Dis.*, 145:114-120, 1991.

Zakynthinos et al., "The load of inspiratory muscles in patients needing mechanical ventilation," *Am. J. Resp. and Crit. Care Med.*, 152:1248-1255, 1995.

\* cited by examiner

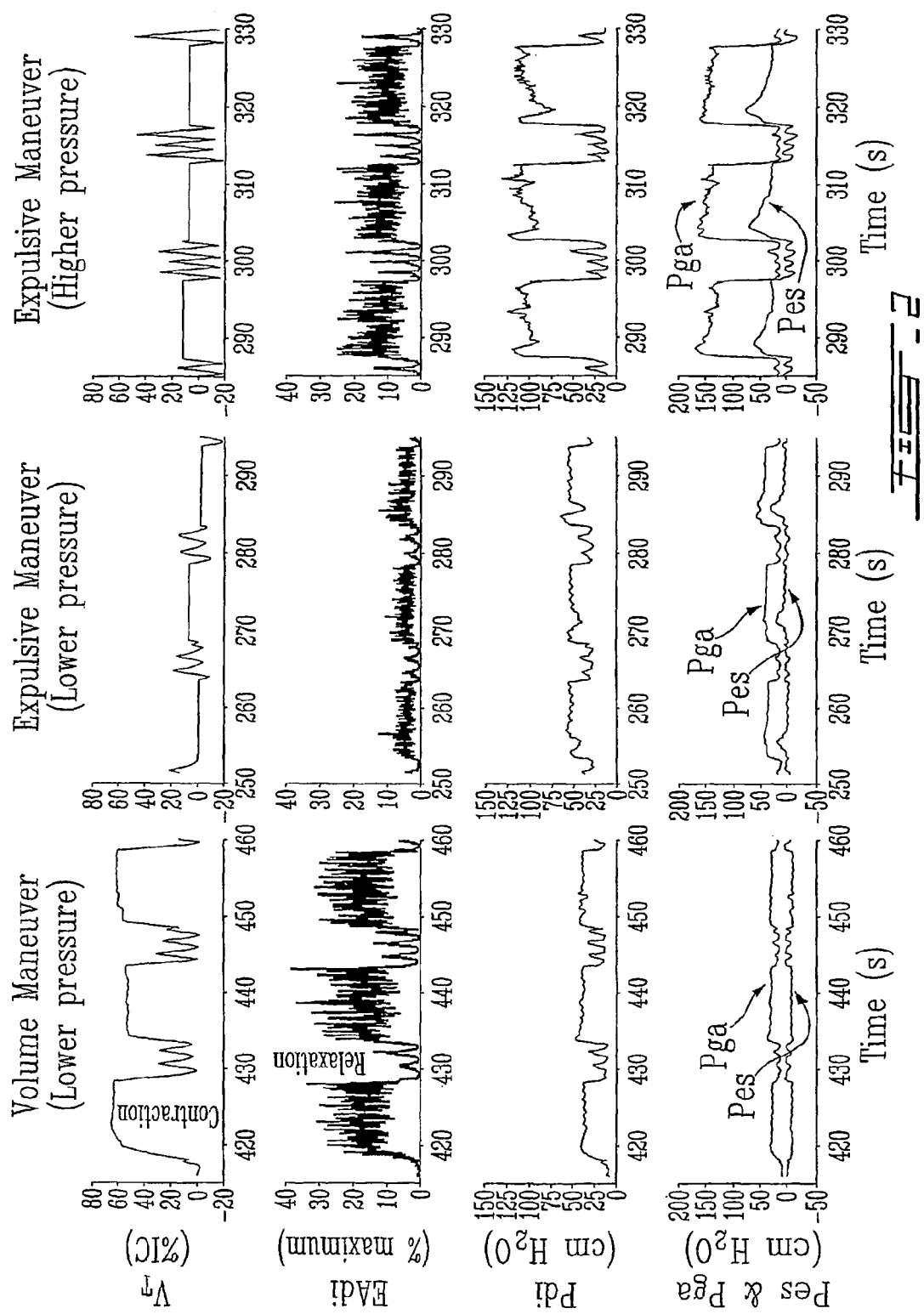

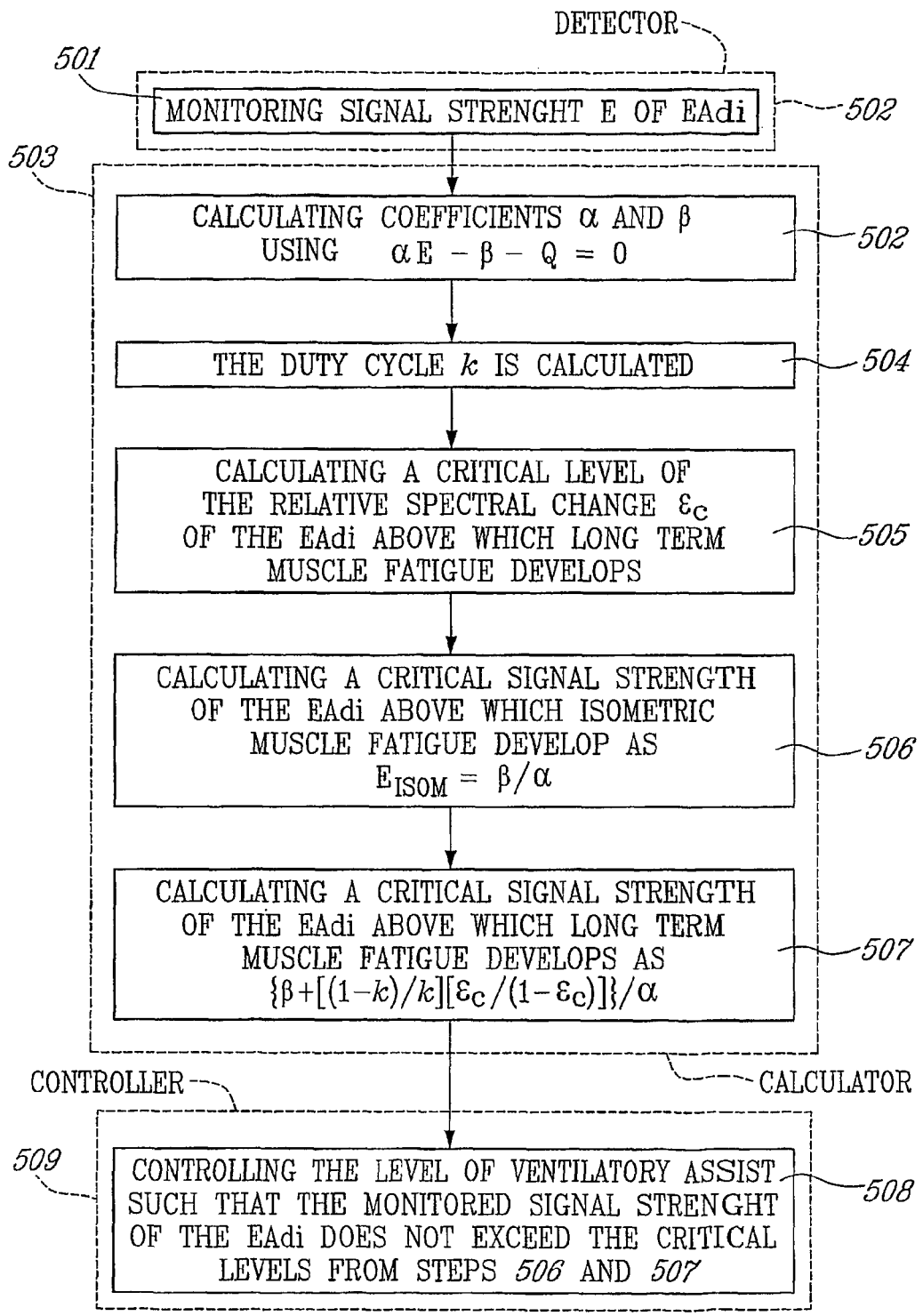

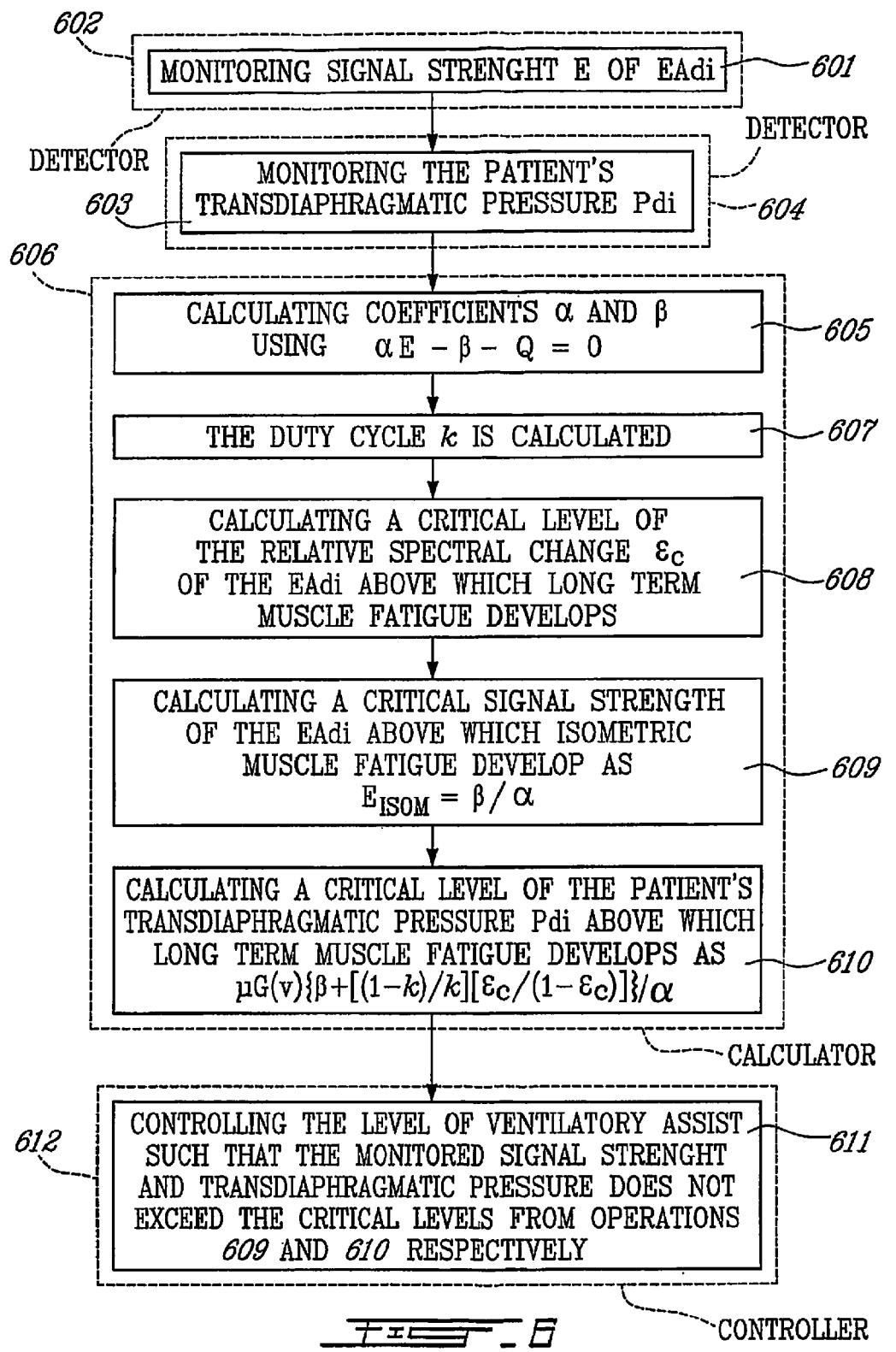

METHOD AND DEVICE USING MYOELECTRICAL ACTIVITY FOR OPTIMIZING A PATIENT'S VENTILATORY ASSIST

This application is a national phase application under 35 U.S.C. §371 of International Application No. PCT/CA2005/000217 filed 18 Feb. 2005, which claims priority to U.S. Provisional Patent Application Ser. No. 60/545,577, filed 18 Feb. 2004, the contents of which are incorporated herein by reference in their entirety.

FIELD OF THE INVENTION

The present invention relates to a method and device for determining a level of ventilatory assist to a ventilator-dependent patient.

BACKGROUND OF THE INVENTION

Both the tension developed by a patient's muscle [34] and the duration of the muscle contraction [2] are factors that lead to respiratory muscle fatigue; these two factors can be expressed by indices such as the tension-time index [3] and the pressure-time product [10, 20, 32, 35]. Bellemare and Grassino [3] showed a direct inverse relationship exists between the time of endurance of a fatiguing diaphragm contraction and the rate of decay of the ratio of the high to low spectral components (H/L) of the electrical activity EAdi of the patient's diaphragm, indicating that these two values are indicative of progressive failure to sustain load. The force exerted by the muscle has been shown to be directly related to the rate of decay of the power spectrum center frequency or the rate of decay of the above mentioned ratio H/L, and the level at which this power spectrum center frequency or ratio H/L plateaus [16, 21, 28]. Such shifts in the power spectrum reflect a reduction in the muscle action potential conduction velocity [28, 38, 39], and constitute an early indication that, at the cellular level, these breathing patterns cannot be maintained indefinitely [3].

Hyperinflation, which impairs the length-tension relationship of the respiratory muscles, i.e. the transformation of the neural activation into a mechanical output or pressure, reduces the capacity of the respiratory muscles to generate pressure (neuromechanical uncoupling), unless the electrical activity EAdi of the patient's diaphragm is increased. Studies have shown that when the inspiratory pressure, flow and duty cycle remain constant, increases in end-expiratory lung volume (EELV) promote reductions in endurance time [33, 44] and sustainable pressure [11]. In an animal model, Tzelepi's et al [44] proposed that, under these conditions, diaphragm shortening would require greater excitation to generate a given sub-maximum tension, and that this increased excitation might account for the greater contractile muscle fatigability observed at shorter muscle length.

The level of partial ventilatory assist, with the aim to ensure adequate pulmonary ventilation while preserving inspiratory muscle function, is generally set on an empirical basis in the clinical setting.

It has been proposed that an optimal level of partial ventilatory assist could be determined from the lowest stable breathing frequency $f_B$ achieved, i.e. without bradypnea or apnea. In patients, this corresponded to 16.4 bpm (breaths per minute) and was associated with a tidal volume $V_T$ of 11.8 ml/kg. However, mechanical lung modeling in that study demonstrated that such a level of support actually resulted in a total unloading of the respiratory muscles.

Others have defined an optimal level of partial ventilatory assist as that which produces the lowest swings of transdiaphragmatic pressure $P_{di}$ and found that this condition was associated with a breathing frequency $f_B$ of 19.7 bpm and a tidal volume $V_T$ of 11.7 ml/kg. The transdiaphragmatic pressure $P_{di}$ in the latter study was used as a marker of inspiratory effort.

Jubran et al [20] defined an upper bound inspiratory pressure-time product lower than 125 cm $H_2O \cdot s$/min as a desirable level of inspiratory effort to be achieved during partial ventilatory assist. Although arbitrarily determined, this threshold was justified by the fact that it corresponded to a tension-time index $TT_{di}$ well below that considered to indicate impeding inspiratory muscle fatigue. The study found a high variability in pressure-time products between patients and demonstrated that a breathing frequency $f_B < 30$ bpm and a tidal volume $V_T$ of 0.6 L were better determinants of an optimal level of inspiratory effort during partial ventilatory assist. Based on these breathing pattern findings, it is likely that the level of respiratory muscle unloading provided by this method of optimizing partial ventilatory assist was lower than that of the above discussed studies.

Brochard et al [8] defined an optimal partial ventilatory assist level as the lowest level of ventilatory assist, which when implemented, maintained the highest level of diaphragmatic electrical activation without the occurrence of fatigue as evaluated via power spectrum analysis of the electrical activity $EA_{di}$ Of the patient's diaphragm. Interestingly, such levels of partial ventilatory assist were associated with a breathing frequency $f_B$ of 20-27 bpm and a tidal volume $V_T$ of 8.0 ml/kg, these values being similar to those later reported by Jubran et al [20].

SUMMARY OF THE INVENTION

In accordance with the present invention, there is provided a method for determining a level of ventilatory assist to a ventilator-dependent patient, comprising: calculating a critical threshold of a respiration-related feature, wherein fatigue of a respiratory muscle of the ventilator-dependent patient develops when the critical threshold is reached by the respiration-related feature; and controlling the level of ventilatory assist to the ventilator-dependent patient in relation to the critical threshold of the respiration-related feature so as to prevent fatigue of the patient's respiratory muscle.

The present invention also relates to a device for determining a level of ventilatory assist to a ventilator-dependent patient, comprising: a calculator of a critical threshold of a respiration-related feature, wherein fatigue of a respiratory muscle of the ventilator-dependent patient develops when the critical threshold is reached by the respiration-related feature; and a controller of the level of ventilatory assist to the ventilator-dependent patient in relation to the critical threshold of the respiration-related feature so as to prevent fatigue of the patient's respiratory muscle.

The foregoing and other objects, advantages and features of the present invention will become more apparent upon reading of the following non-restrictive description of illustrative embodiments thereof, given by way of example only with reference to the accompanying drawings.

BRIEF DESCRIPTION OF THE DRAWINGS

In the appended drawings:

FIG. 2 are illustrative examples of tracings of tidal volume $V_T$, diaphragm electrical activity EAdi, transdiaphragmatic pressure $P_{di}$, esophageal pressure $P_{es}$, and gastric pressure ($P_{ga}$) measured on a subject during "volume" maneuvers and "expulsive" maneuvers;

FIG. 5 is a flow chart and block diagram of a first non-restrictive illustrative embodiment of the method and device according to the present invention, for determining a level of ventilatory assist to a ventilator-dependent patient; and FIG. 6 is a flow chart and block diagram of a second non-restrictive illustrative embodiment of the method and device according to the present invention, for determining a level of ventilatory assist to a ventilator-dependent patient.

DETAILED DESCRIPTION OF THE ILLUSTRATIVE EMBODIMENTS

A study was conducted to determine in humans whether an increased electrical activity EAdi of a patient's diaphragm, with neuromechanical uncoupling, promotes greater reductions in the center frequency $CF_{di}$ of the diaphragm's electrical activity EAdi, when the diaphragm pressure-time product $PTP_{di}$ is kept constant. An additional aim of the study was to establish the extent to which the diaphragm pressure-time product $PTP_{di}$ needs to be increased, in the presence of normal neuromechanical coupling, in order to reproduce the drop in center frequency $CF_{di}$ observed with uncoupling.

More specifically, the study evaluated whether increased diaphragm activation induced by an increased lung volume promotes increased drops in the center frequency $CF_{di}$ of the diaphragm's electrical activity EAdi when the diaphragm pressure-time product $PTP_{di}$ is kept constant. Five healthy subjects performed runs of intermittent quasi-static diaphragmatic contractions with a fixed breathing pattern. In separate runs, the subjects targeted transdiaphragmatic pressures $P_{di}$ by performing end-inspiratory holds at total lung capacity with the glottis open (neuromechanical uncoupling), and at end-expiratory lung volume by performing expulsive maneuvers (no neuromechanical uncoupling). Diaphragm activation and pressures were measured with an electrode array and with balloons, respectively, mounted on an esophageal catheter. Reproduction of a transdiaphragmatic pressure $P_{di}$ of ≈31 cm $H_2O$ during neuromechanical uncoupling increased lung volume to 77.5% of the inspiratory capacity, increased the diaphragm's electrical activity EAdi from 25% to 61% of the maximum and resulted in a 17% greater drop in center frequency $CF_{di}$. In order to reproduce, in the absence of neuromechanical uncoupling, the decrease in center frequency $CF_{di}$ observed during neuromechanical uncoupling, a two-fold increase in transdiaphragmatic pressure $P_{di}$ and diaphragm pressure-time product $PTP_{di}$ was required. It was concluded that a constant diaphragm pressure-time product $PTP_{di}$ does not necessarily result in a center frequency $CF_{di}$ of the diaphragm's electrical activity EAdi that remains stable when activation is increased.

METHODS

Subjects

Five healthy subjects (1 female, 4 males) with a mean age of 40.6±8.0 years participated in the study. The study was approved by the Scientific and Ethical Committees of Sainte-Justine's Hospital and all subjects gave their informed consent.

Experimental Protocol

Figure 1:
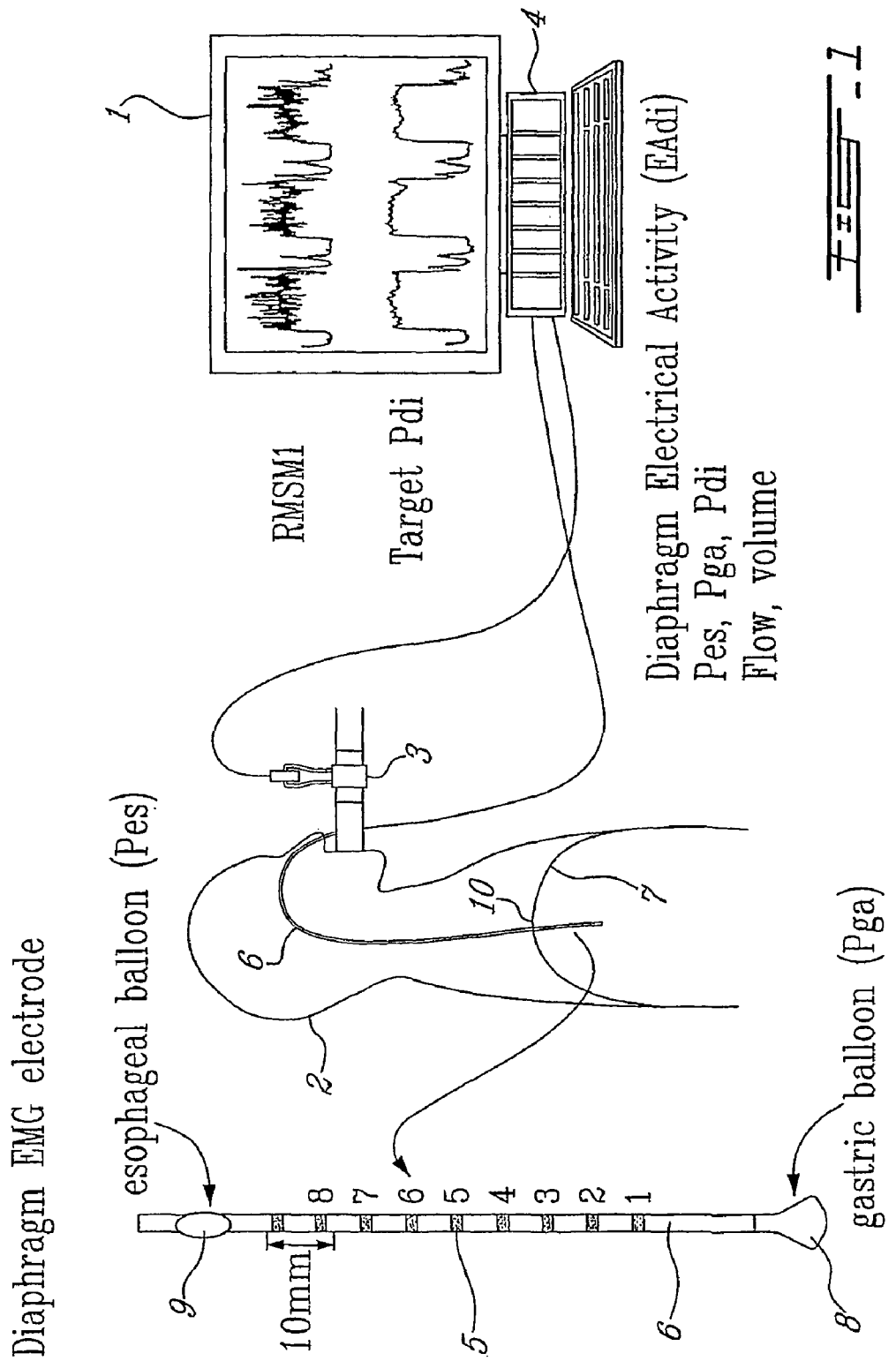
FIG. 1 is a schematic representation of a non-limitative example of experimental set-up for measuring diaphragm's electrical activity EAdi, esophageal pressure $P_{es}$, gastric pressure $P_{ga}$, respiratory airflow and tidal volume $V_T$, and for displaying on line the target transdiaphragmatic pressure $P_{di}$ and the root-mean-square (RMS) of the diaphragm's electrical activity EAdi.
Figure 3A:
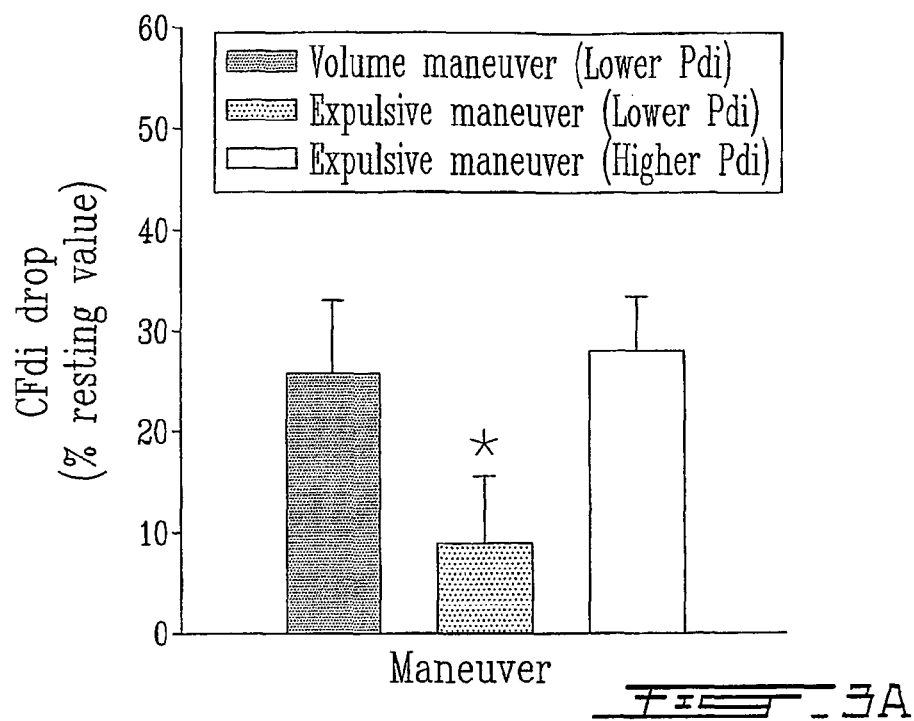
FIG. 3 are examples of bar graphs displaying drops in center frequency $CF_{di}$, targeted levels of transdiaphragmatic pressure $P_{di}$, diaphragm pressure-time product $PTP_{di}$ and the associated diaphragm's electrical activity EAdi observed during volume and lower-pressure expulsive and higher pressure expulsive maneuvers.
Figure 3B:
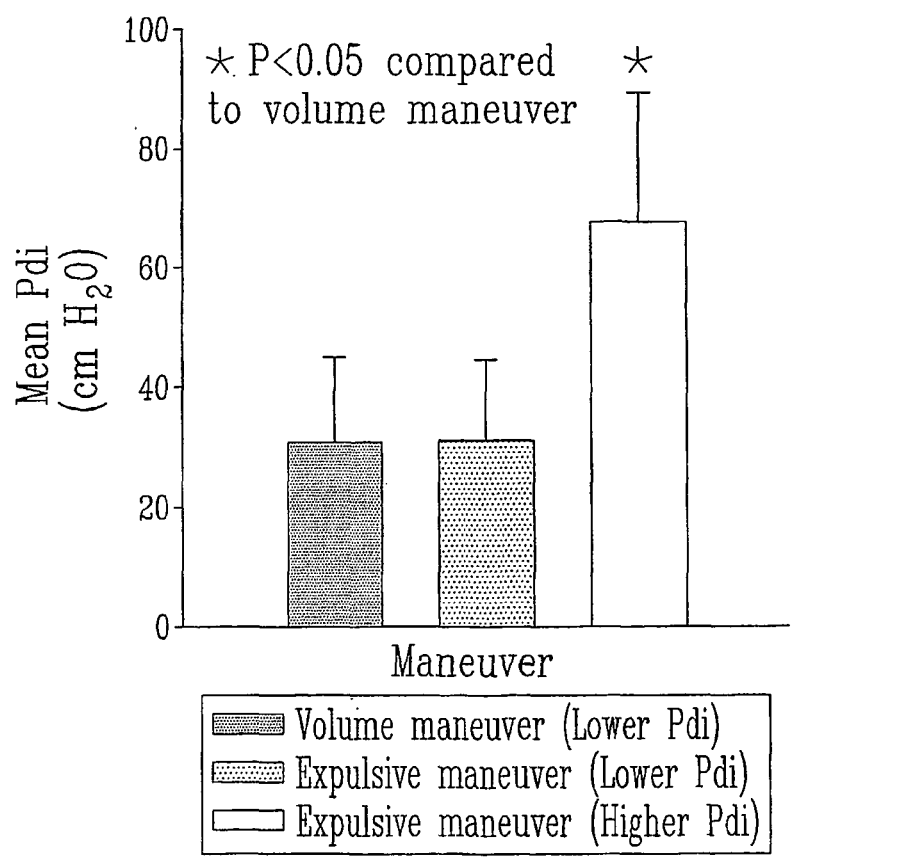
Figure 3C:
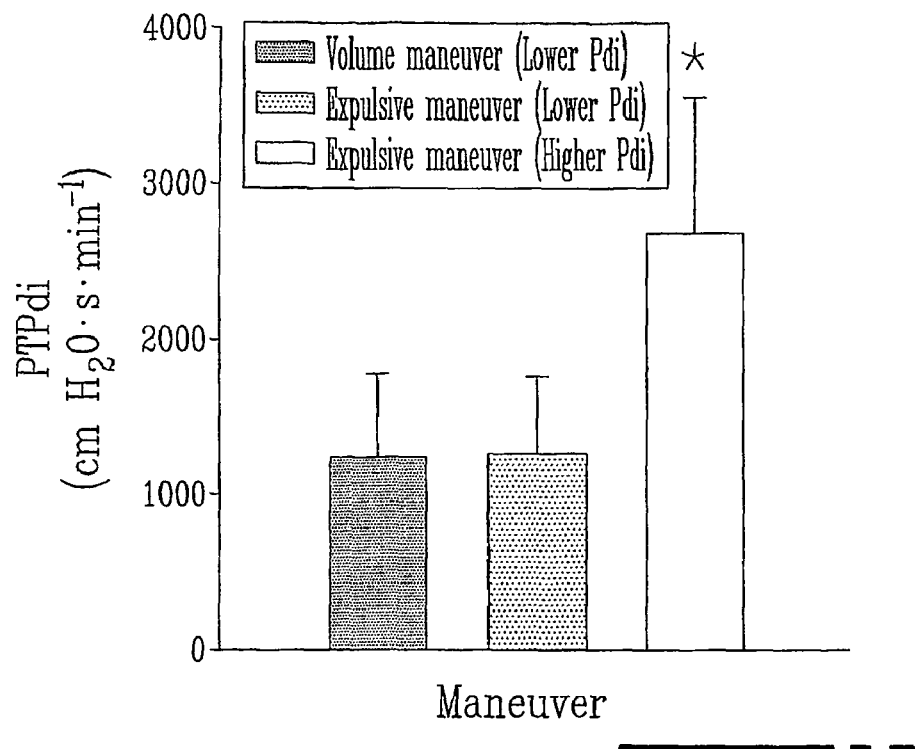
Figure 3D:
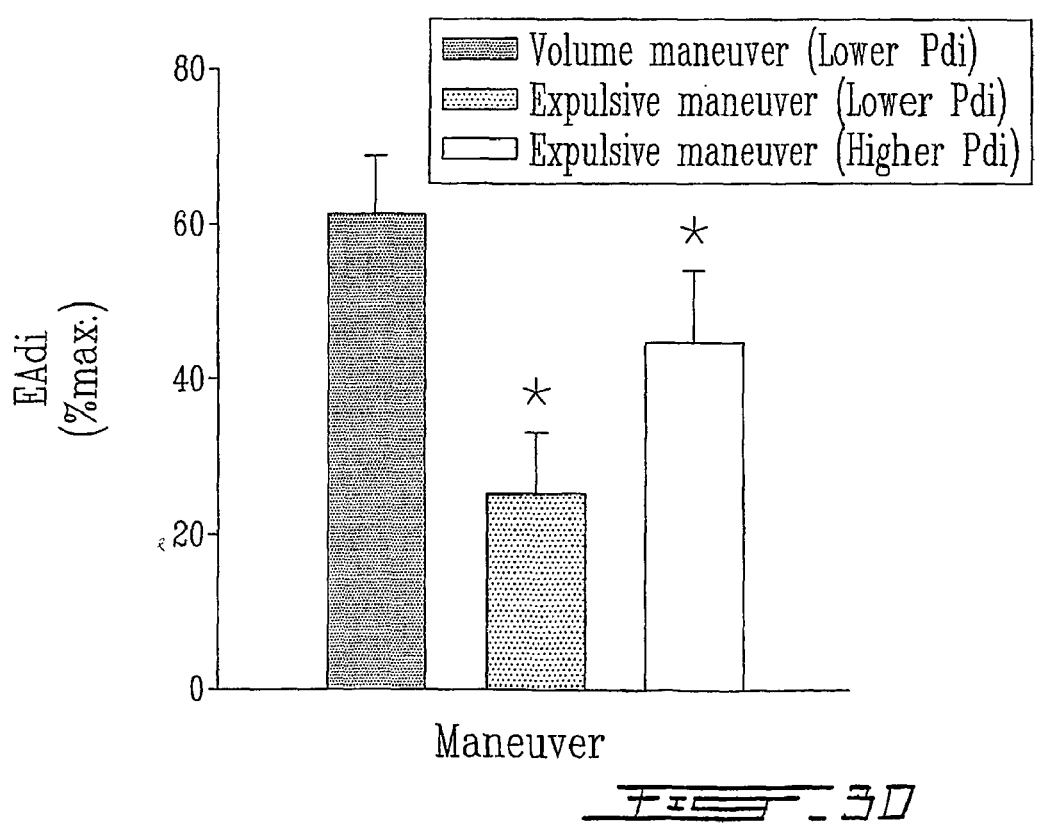

FIG. 1 is a schematic representation of a non-limitative example of experimental set-up. On the left, an esophageal catheter-mounted multi-electrode array 5 is used to measure diaphragm's electrical activity EAdi and balloons 8 and 9 mounted on the catheter on opposite sides of the electrode array 5 are used to measure esophageal pressure $P_{es}$ and gastric pressure $P_{ga}$. The catheter 6 was passed trans-nasally and positioned at the gastro-esophageal junction 10. Respiratory airflow was measured with a pneumotachograph 3 and tidal volume $V_T$ was obtained by integrating inspiratory flow. On the right, the target transdiaphragmatic pressure $P_{di}$ and the root-mean-square (RMS) of the diaphragm's electrical activity EAdi are displayed on line.

Referring to FIG. 1, each human subject 2, while seated in an upright chair (not shown) and facing a the monitor 1 of a computer 4, performed repeated maximal inspirations to total lung capacity (TLC) in order to obtain three reproducible voluntary maximum values for the diaphragm's electrical activity EAdi. Each subject 2 was subsequently asked to perform intermittent, near-isometric diaphragmatic contractions of 10 seconds duration, separated by 5 seconds relaxation periods during which free breathing was allowed. With visual feedback of the transdiaphragmatic pressure $P_{di}$ on the monitor 1 of the computer 4 a low level of transdiaphragmatic pressure $P_{di}$ was targeted during two runs, while a higher level of transdiaphragmatic pressure $P_{di}$ was targeted during a third run. The duty cycle was imposed by a sound signal, and each run lasted until a plateau in center frequency $CF_{di}$ was reached, or until the subject was no longer able to maintain the target transdiaphragmatic pressure $P_{di}$.

FIG. 2 are examples of tracings of tidal volume $V_T$, diaphragm electrical activity EAdi, transdiaphragmatic pressure $P_{di}$, esophageal pressure $P_{es}$, and gastric pressure $P_{ga}$ measured in one subject during "volume" maneuvers and "expulsive" maneuvers performed during the hereinafter reported study. The "volume" maneuver consisted of an end-inspiratory hold at an increased lung volume, which resulted in the generation of a low $P_{di}$ (left tracing), whereas the two expulsive maneuvers were performed at end-expiratory lung volume targeting a lower $P_{di}$ (middle tracing) and higher $P_{di}$ (right tracing).

In order to obtain two different levels of diaphragm's electrical activity EAdi for the same target transdiaphragmatic pressure $P_{di}$, each subject 2 was instructed to perform two different maneuvers:

1. Volume maneuver: the subjects inspired close to their total lung capacity (TLC) and produced a given level of transdiaphragmatic pressure $P_{di}$ (FIG. 2; left tracing). The transdiaphragmatic pressure $P_{di}$ was maintained at this lung volume with the glottis open.

2. Expulsive maneuver: the subjects performed expulsive maneuvers in order to generate a target transdiaphragmatic pressure $P_{di}$. All expulsive maneuvers were performed at end-expiratory lung volume (EELV) at lower and higher transdiaphragmatic pressures $P_{di}$ (FIG. 2, middle and right tracings).

After having initially performed a volume maneuver run, each subject 2 then performed two expulsive maneuver runs. One expulsive maneuver run targeted a transdiaphragmatic pressure $P_{di}$ (lower pressure) similar to that observed during the volume maneuver but requiring less diaphragm's electrical activity EAdi, while another expulsive maneuver run targeted an increased transdiaphragmatic pressure $P_{di}$ (higher pressure) to reproduce the center frequency $CF_{di}$ observed during the volume maneuver run. The volume maneuver was subsequently repeated once for retest purpose. The subject rested for 20 minutes between subsequent runs.

Instrumentation

Using the set-up of FIG. 1:

airflow and tidal volume were measured by a computer 4 through a pneuinotachograph 3;

electrical activity EAdi of the patient's diaphragm was measured by the computer 4 through the linear array 5 of electrodes mounted on an esophageal catheter 6 inserted through the patient's nostril (or patient's mouth) until the electrode array 5 is positioned in the gastro-esophageal junction 10 of the patient's diaphragm 7;

esophageal $P_{es}$ and gastric $P_{ga}$ pressures were measured by the computer 4 through the gastric 8 and esophageal 9 balloons mounted on the catheter 6 on opposite sides of the array 5 of electrodes; and the transdiaphragmatic pressure $P_{di}$ was obtained by the computer 4 by subtracting the measured esophageal pressure $P_{es}$ from the measured gastric pressure $P_{ga}$.

On-Line Automatic Processing of Diaphragm's Electrical Activity EAdi

The diaphragm's electrical activity EAdi, more specifically a root-mean-square (RMS) EAdi signal was acquired, processed and displayed on-line using a standardized methodology [4, 36, 41]. The center frequency $CF_{di}$ was evaluated for signal quality using established indices and criteria in accordance with a method disclosed by Sinderby et al [40]. To avoid influence of power spectral shifts on the EAdi signal strength, the RMS EAdi signal was calculated on the spectral moment of order 1 (M1) which is insensitive to conduction velocity [6] (see upper trace on the computer monitor 1. For more extensive review reference is made to Aldrich et al [1].

Off-Line Signal Analysis

Inspiratory duration $T_i$, total breath duration $T_{tot}$, and breathing frequency $f_B$, diaphragm's electrical activity EAdi and pressures $P_{es}$ and $P_{ga}$ were determined using the transdiaphragmatic pressure $P_{di}$. The diaphragm pressure-time product $PTP_{di}$ was obtained by multiplying (i) the under-the-curve area subtended by the $P_{di}$ signal by (ii) the breathing frequency $f_B$. The amplitude of the signal of the diaphragm's electrical activity EAdi was expressed as a percentage of the voluntary maximum diaphragm's electrical activity EAdi obtained from TLC maneuvers [37]. Variables were compared between each of the maneuvers performed using one-way repeated measurements analysis of variance (ANOVA) and post hoc contrasts of significant effects were performed using the Student-Newman-Keuls test. Test-retest reliability of the $P_{di}$, EAdi and $CF_{di}$ values obtained during the volume and expulsive maneuvers was evaluated by calculating the interclass correlation coefficient (ICC).

RESULTS

The subjects were able to perform all maneuvers and maintain the imposed duty cycle (P=0.93; one-way ANOVA) during all protocols (Table 1).

TABLE 1

Breathing pattern and targeted $P_{di}$ values during the three maneuvers performed

| Subject | Volume maneuver | | | Expulsive maneuver Lower pressure | | Expulsive maneuver Higher pressure | |
|---|---|---|---|---|---|---|---|
| | Ti/Ttot | $V_T$% IC | Pdi | Ti/Ttot | Pdi | Ti/Ttot | Pdi |
| 1 | 0.66 | 89.2 | 47.8 | 0.66 | 45.1 | 0.67 | 77.3 |
| 2 | 0.66 | 65.6 | 25.3 | 0.67 | 26.6 | 0.66 | 93.3 |
| 3 | 0.67 | 68.3 | 10.2 | 0.65 | 11.6 | 0.66 | 39.3 |
| 4 | 0.67 | 88.8 | 38.6 | 0.66 | 39.8 | 0.64 | 77.3 |
| 5 | 0.65 | 75.5 | 34.1 | 0.67 | 35.0 | 0.67 | 50.3 |
| Mean | 0.66 | 77.5 | 31.2 | 0.66 | 31.6 | 0.66 | 67.5 |
| (±SD) | (0.01) | (11.1) | (14.2) | (0.01) | (13.1) | (0.01) | (22.0) |

Values are means for each subject of all the maneuvers performed. Ti/Ttot, duty cycle; $P_{di}$, transdiaphragmatic pressure; $V_T$, tidal volume; IC, inspiratory capacity. All subjects were able to maintain the imposed duty cycle.

FIG. 3 are examples of bar graphs displaying drops in center frequency $CF_{di}$, targeted levels of transdiaphragmatic pressure $P_{di}$, diaphragm pressure-time product $PTP_{di}$ and the associated diaphragm's electrical activity EAdi observed during the three volume and lower-pressure expulsive and higher pressure expulsive maneuvers performed in the study. The bars of the graphs of FIG. 3 are average values obtained for the five subjects (±SD (Standard Deviation)).

Figure 4A:
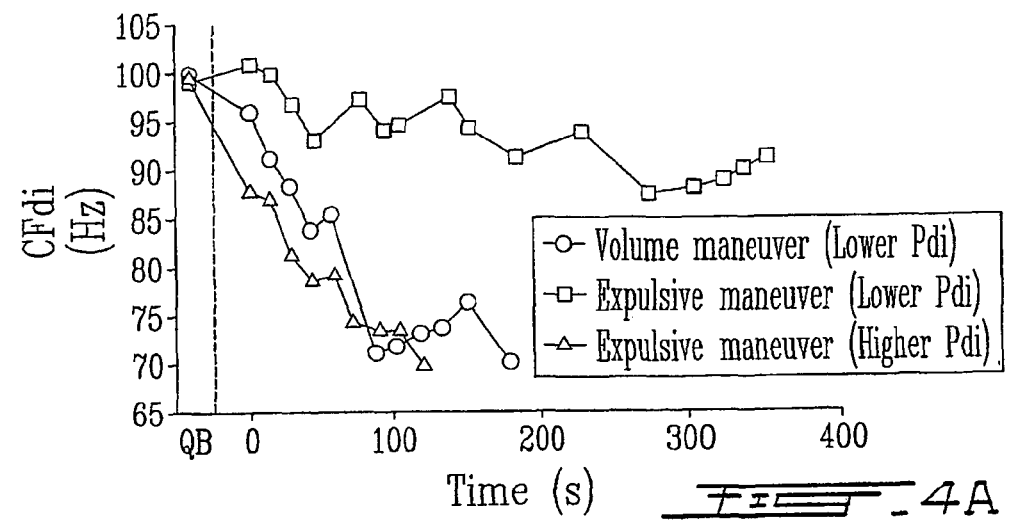
FIG. 4 are examples of graphs from one representative subject showing the center frequency $CF_{di}$, the root-means-square (RMS) of the diaphragm's electrical activity EAdi and the diaphragm pressure-time product $PTP_{di}$ plotted over time during the volume maneuver (circles) and the two expulsive maneuvers at end-expiratory lung volume (EELV), one targeting a lower transdiaphragmatic pressure $P_{di}$ (squares) and the other a higher $P_{di}$ transdiaphragmatic pressure $P_{di}$ (triangles)
Figure 4B:
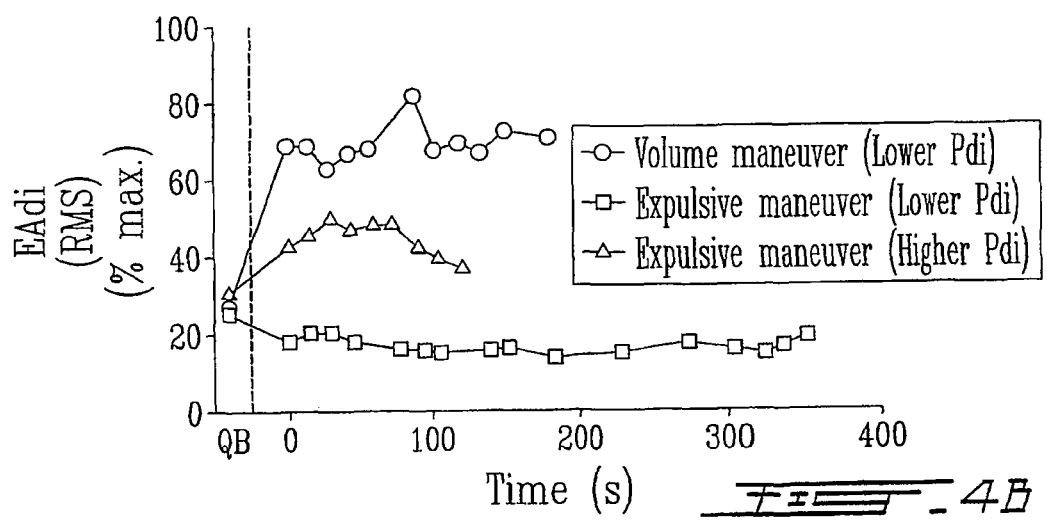
Figure 4C:
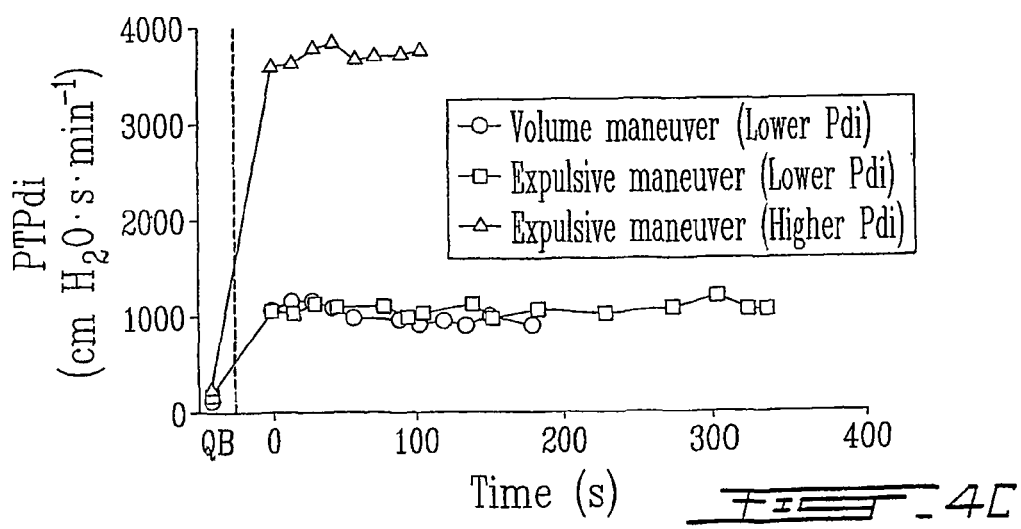

As shown in Table 1 and FIG. 3, subjects were able to achieve and maintain similar target levels of transdiaphragmatic pressure $P_{di}$ during the volume maneuver (high lung volume) and the lower-pressure expulsive maneuver at EELV. During the volume maneuver, subjects inspired to an average of 77.5±11.1% of their inspiratory capacity. In order to generate the same diaphragm pressure-time product $PTP_{di}$ at different lung volumes, the volume maneuver (neuromechanical uncoupling) required a diaphragm's electrical activity EAdi of 60±8% of maximum compared to 25±8% for the expulsive lower-pressure maneuver at EELV. As shown in Table 2 and FIG. 3, despite a matching of the diaphragm pressure-time product $PTP_{di}$, the volume maneuver promoted a 17% larger drop in the center frequency $CF_{di}$ than the expulsive low-pressure maneuver at EELV. FIG. 4 are examples of graphs from one representative subject showing the center frequency $CF_{di}$, the root-means-square (RMS) of the diaphragm's electrical activity EAdi and the diaphragm pressure-time product $PTP_{di}$ plotted over time during the volume maneuver (circles) and the two expulsive maneuvers at end-expiratory lung volume (EELV), one targeting a lower transdiaphragmatic pressure $P_{di}$ (squares) and the other a higher $P_{di}$ transdiaphragmatic pressure $P_{di}$ (triangles). FIG. 4 shows that, for the representative subject, the center frequency $CF_{di}$ declines more rapidly and to a greater extent during the volume maneuver (circles), which required a high diaphragm's electrical activity EAdi for a similar diaphragm pressure-time product $PTP_{di}$, compared to the expulsive lower-pressure maneuver (squares).

TABLE 2

Individual CFdi values observed at end of each maneuver

| Subject | Volume maneuver | Expulsive maneuver Low pressure | Expulsive maneuver High pressure |
|---|---|---|---|
| 1 | 68.3 ± 8.7 | 81.3 ± 7.9 | 61.6 ± 5.6 |
| 2 | 67.4 ± 4.5 | 86.7 ± 8.0 | 70.5 ± 13.2 |
| 3 | 82.0 ± 12.3 | 94.3 ± 7.8 | 71.5 ± 5.0 |
| 4 | 72.8 ± 5.8 | 89.4 ± 6.1 | 73.4 ± 3.1 |
| 5 | 80.4 ± 9.3 | 104.1 ± 4.4 | 83.6 ± 5.4 |
| Mean ± SD | 74.2 ± 6.8 | 91.2 ± 8.6 | 72.1 ± 7.9 |

Values are means for each subject for each of the maneuvers performed.

In order to produce a similar drop in center frequency $CF_{di}$ during the expulsive maneuver at EELV as was observed during the volume maneuver, more than a two-fold increase in the target transdiaphragmatic pressure $P_{di}$ was required. This was associated with an increase in diaphragm's electrical activity EAdi from 25±8% to 44±9% of maximum. As can be seen in FIG. 4, the rate of decline of the center frequency $CF_{di}$ was similar for the volume maneuver (circles) and the expulsive higher-pressure maneuvers (triangles).

Presented in Table 3 are the values of transdiaphragmatic pressure $P_{di}$, diaphragm's electrical activity EAdi and center frequency $CF_{di}$ for the test-retest of the volume maneuver. During the retest, subjects successfully targeted a transdiaphragmatic pressure $P_{di}$ that was similar to that generated during the initial volume maneuver (ICC=0.95). The diaphragm's electrical activity EAdi was also similar (ICC=0.93) as was the drop in center frequency $CF_{di}$ (ICC=0.98).

DISCUSSION

The study evaluated intermittent static contractions maintained at two different lung volumes, in order to examine the effect of altered neuromechanical coupling and increased diaphragm electrical activation, on diaphragm sarcolemma excitability, assessed by changes in center frequency $CF_{di}$. It was found that, for a given targeted diaphragm pressure-time product $PTP_{di}$, the drop in center frequency $CF_{di}$ was greater when the diaphragm's electrical activity EAdi was increased by neuromechanical uncoupling, suggesting that the level of muscle activation influences the center frequency $CF_{di}$.

Studies on the canine diaphragm have demonstrated that changes in center frequency $CF_{di}$ are associated with changes in the mean action potential conduction velocity (APCV) [38], confirming previous mathematical models [29]. During muscle contractions, both center frequency $CF_{di}$ and muscle fiber APCV depend to a smaller extent on the cable properties of the fiber [38, 39], and to a larger extent on the muscle membrane excitability [17, 18, 29, 39]. The excitability of the muscle fiber membrane is dependent on the trans-membrane gradient of potassium, and with increased muscle activation, efflux of potassium increases. In order to defend the extracellular potassium concentration and hence, the membrane potential, the cell depends on the re-uptake of potassium, e.g. via the ATP (Adenosine TriPhosphate) dependent sodium/potassium pump [12], and washout via the blood circulation [25], i.e. diffusion of potassium from the extra-cellular space into the blood stream. Regardless if blood flow is reduced [23, 31, 42], or the muscle activation is increased, as in the present work, the muscles' electrical activity will indicate reduced membrane excitability, by shifts in the power spectrum toward lower frequencies. The center frequency $CF_{di}$ can also be affected by factors such as motor unit territory, number of fibers in the motor unit, dispersion in arrival times of the single contributions in the motor unit signal, dispersion in action potential conduction velocities between motor units that can cause the diaphragm's electrical activity EAdi power spectrum to shift [4, 29]. However, given that these influences are minor in healthy muscles [30] and given that the test situation did not allow for much variability in the contractile pattern, it is unlikely that these influences had more than a minor impact on the results.

In the study, a constant transdiaphragmatic pressure $P_{di}$ was targeted with a constant duty cycle at two different lung

TABLE 3

Test-retest of the volume maneuver

| | $CFdi_o$ (Hz) | | CFdi (Hz) | | EAdi (% max) | | Pdi (cm $H_2O$) | |
|---|---|---|---|---|---|---|---|---|
| Subject | Vol 1 | Vol 2 | Vol 1 | Vol 2 | Vol 1 | Vol 2 | Vol 1 | Vol 2 |
| 1 | 90.4 | 93.1 | 68.3 | 66.2 | 46.5 | 38.1 | 47.8 | 44.6 |
| 2 | 102.5 | 108.2 | 67.4 | 65.7 | 42.4 | 44.4 | 38.6 | 38.3 |
| 3 | 94.7 | 100.3 | 82.0 | 84.7 | 49.8 | 55.0 | 34.1 | 30.7 |
| 4 | 99.7 | 99.5 | 72.6 | 72.1 | 51.3 | 50.6 | 36.5 | 35.8 |
| Mean | 96.8 | 100.3 | 72.8 | 71.9 | 66.7 | 65.0 | 25.3 | 29.5 |
| (±SD) | (5.4) | (6.2) | (6.7) | (8.8) | (10.7) | (11.9) | (9.4) | (7.0) |
| ICC | 0.94 | | 0.98 | | 0.93 | | 0.95 | |

EAdi, diaphragm electrical activity calculated as root-mean-square;
$CFdi_o$, baseline center frequency determined during resting breathing;
CFdi plateau value of the center frequency at the end of the volume maneuver;
$P_{di}$, transdiaphragmatic pressure;
Vol 1, first volume maneuver performed;
Vol 2, second volume maneuver performed;
ICC, interclass correlation coefficient.

volumes, and it was therefore assumed that transdiaphragmatic pressure $P_{di}$ hindrance to blood flow under those conditions remained relatively similar at the different muscle lengths [19]. However, in order to achieve the same target transdiaphragmatic pressure $P_{di}$ at an increased lung volume, diaphragm's electrical activity EAdi was increased, which represents an increase in energy demand/consumption as well as increased metabolic output (e.g. potassium efflux) from the cell. As can be seen in FIG. 3, the rate of decline of $CF_{di}$ at increased lung volume was significantly higher than that observed when the same pressure was targeted at FRC (doubling of transdiaphragmatic pressure $P_{di}$ at the same lung volume) with lower diaphragm's electrical activity EAdi. Vitro studies have also demonstrated that increased activation (i.e. demand), accomplished by increasing stimulation frequency of a muscle shortened to 70% of its optimum length, in order to obtain the same tension generated at optimum length, resulted in an increased fatigue in the shortened muscle [14]. The current study therefore demonstrates that the higher diaphragm activation required for generating the target transdiaphragmatic pressure $P_{di}$ at an increased lung volume (neuromechanical uncoupling) influences the rate/extent to which center frequency $CF_{di}$ decays. Further theoretical evidence for the impact of neuromechanical uncoupling on the center frequency $CF_{di}$ is provided in the following description.

In the absence of neuromechanical uncoupling, an increase in transdiaphragmatic pressure $P_{di}$ is always associated with an increase in diaphragm's electrical activity EAdi. In the above reported study, doubling of transdiaphragmatic pressure $P_{di}$ at the same lung volume (FRC) was associated with an increase in diaphragm's electrical activity EAdi from 25% to 44% of the maximum. Beck et al [6] showed that diaphragm's electrical activity EAdi in absolute values is closely related to transdiaphragmatic pressure $P_{di}$, such that activation increases (i.e. energy demand increases) when pressure increases (i.e. energy supply decreases). However, this relationship is altered when the muscle length changes. In such a circumstance, the transdiaphragmatic pressure $P_{di}$ continues to reflect diaphragm's electrical activity EAdi only when the transdiaphragmatic pressure $P_{di}$ is normalized to the maximum transdiaphragmatic pressure $P_{di}$ obtained at each corresponding lung volume [6]. It was previously shown that when the same diaphragm's electrical activity EAdi is targeted at different lung volumes, the higher resulting transdiaphragmatic pressure $P_{di}$ generated at FRC promotes a greater drop in center frequency $CF_{di}$ than does the lower pressure produced at the higher lung volume [42]. Such results indicate that for a given neural activation, an increase in force or transdiaphragmatic pressure $P_{di}$ reduces diaphragm excitability. Consequently, the use of the $TT_{di}$ and pressure-time product as indices for predicting changes in the excitability of the diaphragm sarcolemma (as reflected by center frequency $CF_{di}$) is limited to conditions of constant neuromechanical coupling, where the diaphragm force generating capacity remains unaltered.

Consistent with previous studies [3, 16, 21, 28], doubling of the target transdiaphragmatic pressure $P_{di}$ at FRC in the present study increased the rate of decline of the center frequency $CF_{di}$ as well as the level to which it declined (FIGS. 3 and 4). This is partially explained by the increase in diaphragm's electrical activity EAdi, as discussed above. However, it is also partially explained by the fact that:

i) diaphragm contractions with a higher transdiaphragmatic pressure $P_{di}$ tend to hinder blood flow (i.e. energy supply) relatively more than contractions producing a lower transdiaphragmatic pressure $P_{di}$ [19]; and ii) impaired blood flow to a muscle has the propensity to promote shifts in the electromyographic power spectrum toward lower frequencies [22, 30].

Methodological and Technical Aspects

In the study the contraction and relaxation periods were maintained at a fixed duration and therefore any potential influence of duty cycle on muscle function [2, 22] was controlled for. It must be emphasized that accurate physiological measurement of the center frequency $CF_{di}$ depends on being able to control for:

(a) changes in muscle-to-electrode distance;
(b) electrode positioning with respect to the muscle fiber direction and location;
(c) electrode configuration;
(d) signal to noise ratio;
(e) influence of cross-talk from other muscles (including the heart and the esophagus); and
(f) electrode movement-induced artifacts [7, 36, 38, 39, 40].

In the study, the technology used to measure the power spectrum of the diaphragm's electrical activity EAdi spectrum included means for minimizing these influences [1, 36, 40]. The findings that evoked muscle action potentials are influenced by changes in lung volume [5, 15] have contributed to the assumption of a potential-inherent inaccuracy of measured amplitudes of the diaphragm's electrical activity EAdi [5, 15] and the center frequency $CF_{di}$ [5]. However, during mild voluntary muscle contractions that do not alter diaphragm membrane excitability, it has been shown that chest wall configuration/lung volume and changes in muscle length have no effect on diaphragm's electrical activity EAdi and center frequency $CF_{di}$ [5, 6, 7, 17, 39]. Therefore the above-discussed effect of chest wall configuration/lung volume likely did not have an impact on the results.

Another factor that could have influenced the results of the study is the difference in partitioning the esophageal and gastric pressures for the same transdiaphragmatic pressure $P_{di}$ during the various maneuvers. In a previous study [42], where subjects targeted the same diaphragm's electrical activity EAdi at higher and lower lung volumes, greater decreases in center frequency $CF_{di}$ were consistently observed at EELV (higher transdiaphragmatic pressure $P_{di}$), regardless of whether subjects performed an expulsive (i.e. transdiaphragmatic pressure Pd generated mainly by gastric pressure) or a Mueller maneuver (i.e. transdiaphragmatic pressure $P_{di}$ generated mainly by esophageal pressure) at EELV [42]. In a pilot trial to that study (unpublished observations), it was found that diaphragm contractions generating identical transdiaphragmatic pressure $P_{di}$, duty cycle and diaphragm's electrical activity EAdi, produced the same trajectory of decrease in center frequency $CF_{di}$, whether subjects performed expulsive or Mueller maneuvers. Therefore, it is not believed that differences in the partitioning of the esophageal and gastric pressures during the volume and expulsive maneuvers in the current study had an effect on the outcomes observed.

Clinical Implications

The results of the above reported study have direct implications to subjects or patients being weaned from mechanical ventilation. It is well known that patients undergoing a weaning trial may demonstrate dynamic changes in EELV (dynamic hyperinflation) [43], which similar to the study would alter the neuromechanical coupling of the diaphragm. In order to compensate for this uncoupling (i.e. maintain the same transdiaphragmatic pressure $P_{di}$), the patient would need to increase diaphragm activation. The combination of an increased activation of the patient's diaphragm, with an elevated transdiaphragmatic pressure $P_{di}$ would, according to the present study, lead to decreased center frequency $CF_{di}$ (excitability), and possibly an increased respiratory effort sensation [42]. Shifts in the H/L ratio of the power spectrum of the diaphragm's electrical activity EAdi have been reported in patients with respiratory failure in whom ventilatory assistance is removed [8, 13]. However, given that diaphragm weakness is prevalent in mechanically ventilated patients [24], it remains to be determined what combined levels of diaphragm's electrical activity EAdi and transdiaphragmatic pressure $P_{di}$ would affect center frequency $CF_{di}$.

CONCLUSION

The above-reported study shows that diaphragm activation can be used to determine diaphragm membrane excitability and changes in center frequency $CF_{di}$. Furthermore it shows that the diaphragm pressure-time product $PTP_{di}$ and tension-time index $TT_{di}$ cannot be considered as valid reflections of diaphragm energy consumption and/or sarcolemma excitability when neuromechanical coupling is altered.

With data from the above investigation or study, the diaphragmatic muscle force can be estimated from measurements of the diaphragm's electrical activity EAdi in two ways.

A first way for estimating the diaphragmatic muscle force uses the following equation:

$$F = \mu EAdi \quad (1)$$

where F is the diaphragmatic muscle force, $\mu$ is a proportionality constant, and EAdi is a measure of the signal strength of the electrical activity of the patient's diaphragm. Here the square root of the first power spectral moment is used since it represents the signal strength, which has been compensated for the influence of changes in the propagation velocity of the myoelectric action potentials [29].

A second way for estimating the diaphragmatic muscle force uses the spectral changes during diaphragm contraction. For a forceful periodic muscle loading, the center frequency CFdi decreases from an initial center frequency $CF_0$ to a final plateau value $CF_\infty$ according to the equation [26]:

$$CF_\infty = CF_o(1-\kappa)T_D/[(1-\kappa)T_D + \kappa T_R] \quad (2)$$

where $\kappa$ is the duty cycle, i.e. the inspiration time in relation to the total time period, and $T_R$ is the center frequency $CF_{di}$ recovery time constant pertaining to an approximately exponential time curve which is rather independent of the muscle force [9]. The symbol $T_D$ denotes the time constant for the decrease in center frequency $CF_{di}$, which is related to the muscle force as [27]:

$$T_D = \eta/(F-F_C) \quad (3)$$

In this equation $\eta$ is a proportionality constant and $F_C$ is a critical force level above which muscle fatigue starts to develop. Equation (2) is rearranged to obtain the experimentally determinable quantity:

$$Q = T_R/T_D = [(1-\kappa)/\kappa][(CF_0-CF_\infty)/CF_\infty] \quad (4)$$

Equations (3) and (4) then give:

$$F = F_C + Q\eta/T_R \quad (5)$$

Making equal the two force estimates of equations (1) and (5) the following relation is found:

$$\alpha EAdi - \beta - Q = 0 \quad (6)$$

where $$\alpha = \mu T_R/\eta \quad (7)$$

and $$\beta = F_C T_R/\eta \quad (8)$$

Relation (6) represents a set of three equations (for the three experimental conditions) with two unknowns. A fitting procedure with data from the following Table 4 with simultaneous minimization of the relative errors in the diaphragm's electrical activity signal strength EAdi and the quantity Q, gives the values $\alpha=0.00417$ and $\beta=0.0419$ with a relative fitting error of 0.24.

TABLE 4

Experimental results and calculated values

| | $P_{di}$ | EAdi | $CF_0$ | $CF\infty$ | Q | Force ratios | | | Geometric factors | | |
|---|---|---|---|---|---|---|---|---|---|---|---|
| | | | | | | $\phi_I$ | $\phi_{II}$ | $\phi_m$ | $\gamma_I$ | $\gamma_{II}$ | $\gamma_m$ |
| | (cm H$_2$O) | (a.u.) | (Hz) | (Hz) | | | | | (cm H$_2$O) | (cm H$_2$O) | |
| Volume Maneuver | 31.2 | 60.9 | 100 | 74.2 | 0.175 | 6.12 | 5.20 | 5.66 | 122 | 144 | 133 |
| Expulsive maneuver (Lower pressure) | 31.6 | 24.9 | 100 | 91.2 | 0.050 | 2.50 | 2.19 | 2.35 | 303 | 347 | 325 |
| Expulsive maneuver (Higher pressure) | 67.5 | 44.3 | 100 | 72.1 | 0.196 | 4.45 | 5.69 | 5.07 | 364 | 285 | 324 |

$P_{di}$, transdiaphragmatic pressure;
a.u., arbitrary units;
EAdi, signal strength of the electrical activity of the diaphragm;
$CFdi_o$, baseline diaphragm center frequency determined during resting breathing;
CFdi, plateau value of the diaphragm center frequency at the end of the maneuver;
Q, ratio of the time constants of CFdi recovery and decline, see equation (5);
$\phi_I$, see equation (9);
$\phi_{II}$, see equation (10);
$\phi_m$, mean of $\phi_I$ and $\phi_{II}$;
$\gamma_I$, see equation (14);
$\gamma_{II}$, see equation (15);
$\gamma_m$, mean of $\gamma_I$ and $\gamma_{II}$.

With $\alpha$ and $\beta$ known, the experimental values of the diaphragmatic muscle force F can be expressed in relation to the critical force level $F_C$ for onset of deterioration of cell excitability, i.e. the critical force level above which muscle fatigue starts to develop. The two ways to describe this are obtained by rearranging equations (1) and (7), and equation (5), respectively, which gives:

$$\phi_I = (F/F_C)_I = \alpha EAdi/\beta \qquad (9)$$

and $$\phi_{II} = (F/F_C)_{II} = 1 + Q/\beta \qquad (10)$$

These quantities have been determined and are listed in Table 4 together with their mean values $\phi_m$.

The observed transdiaphragmatic pressure $P_{di}$ is assumed to be related to the diaphragmatic muscle force F as:

$$P_{di} = FG \qquad (11)$$

where G is a geometrical factor taking into account that the diaphragm muscle changes its shape with the inspired volume. This factor G is thus assumed to be the same during the expulsive maneuvers with lower or higher $P_{di}$ production performed at end-expiratory lung volume. As with the force relations, the transdiaphragmatic pressure $P_{di}$ can be expressed in two ways, relating to the diaphragm's electrical activity signal strength EAdi and to the fatigue induced spectral changes. Combining equations (1), (5), and (11) leads to the following relations:

$$P_{di} = \mu EAdi \, G \qquad (12)$$

and $$Pdi = (F_C + Q\eta/T_R)G \qquad (13)$$

Relations (12) and (13) can be further developed with relations (7) and (8) into the two following relations:

$$\gamma_I = (G\eta/T_R)_I = Pdi/(\alpha EAdi) \qquad (14)$$

and $$\gamma_{II} = (G\eta/T_R)_{II} = Pdi/(\beta+Q) \qquad (15)$$

Numerical values, calculated for the two expressions, are given in Table 4 together with their mean values $\gamma_m$.

From the results listed in Table 4, it can be concluded that the diaphragmatic muscle force F in relation to the critical force level $F_C$ are approximately the same during the volume maneuver and the higher pressure expulsive maneuver, which is also reflected in their deterioration of cell excitability, expressed by the factor Q. During all conditions the diaphragmatic muscle forces F are above the critical force level $F_C$ as shown by values of $\phi_m$ in Table 4. The geometrical dependence, expressed by the factor $\gamma_m$, is obviously the same during lower pressure expulsive maneuver and higher pressure expulsive maneuver, but is much less during the volume maneuver. The ratio between the $\gamma$ values in the volume maneuver and the expulsive maneuvers is about 0.41. Since the $\eta$ values and the $T_R$ values are expected to be independent of the maneuvers, this means that also the factors G have the same ratio. This indicates a much lower efficiency to convert force into pressure during the volume maneuver. The tension time index $TT_{di}$, taking into account the timing and the pressure, is thus not sufficient to describe the complexity of the fatigue development. At least it has to be modified with a volume dependent correction factor. Better, though, are methods reflecting the deterioration of cell excitability and not the mechanical result of the contraction.

Electromyographic and Mechanical Methods to Detect Muscle Fatigue

Based on the above results, techniques to determine critical levels of muscle fatigue during periodic loading (such as respiration) will be described. A number of equations relating certain physiological variables to each other are needed and they will be derived prior to the description of these techniques.

Periodic Muscle Load Characteristics

Consider a periodic muscle loading, such as the respiratory work, in which repeated muscle contractions alternate with muscle relaxations. The periodic muscle loading is characterized by a time period $T_0$ and its two parts: the duration of muscle contraction $T_1$ and the duration of muscle relaxation $T_2$ where:

$$T_0 = T_1 + T_2 \qquad (16)$$

In order to simplify the equations, the duty cycle $\kappa$ is determined as:

$$\kappa = T_1/T_0 \qquad (17)$$

The mean diaphragmatic muscle force developed during the time interval $T_1$ is denoted F.

Myoelectric Changes Due to Fatigue

Isometric fatiguing contractions cause the center frequency CFdi of the diaphragm's electrical activity EAdi diaphragm's electrical activity to decrease exponentially from its resting value $CF_0$ with a time constant $T_F$. During recovery the center frequency CFdi returns gradually to its normal value following an approximately exponential course, described by the recovery time constant $T_R$. It is observed that many other characteristics of the power spectrum of the diaphragm's electrical activity EAdi exhibit the same dependencies such as the median frequency, the zero crossing density, the so-called hi-over-low value, etc. The recovery time constant depends mostly on the density of capillaries in the muscle and is rather insensitive to the exerted force. The fatigue time constant is strongly dependent on the force when it exceeds a certain critical level $F_C$. The relation is:

$$T_F = \eta/(F - F_C) \text{ for } F > F_C \qquad (18a)$$

and $$T_F \to \infty \text{ for } F \leq F_C \qquad (18b)$$

The combination of repeated work and recovery events causes the center frequency CFdi to decrease from the initial value to a final plateau value $CF_\infty$, at which there is a balance between the metabolite production during work and wash-out during recovery. The plateau value is:

$$CF_\infty = CF_0(1-\kappa)T_F/[(1-\kappa)T_F + \kappa T_R] \qquad (19)$$

Introducing the notations:

$$\Delta CF = CF_0 - CF_\infty \qquad (20)$$

and $$\epsilon = \Delta CF/CF_0 \qquad (21)$$

Equation (19) can then be rearranged to read:

$$\kappa = 1/[1 + (T_R/T_F)(\Delta CF/CF_\infty)] \qquad (22)$$

With the notation:

$$Q = T_R/T_F \qquad (23)$$

it is found that:

$$Q = [(1-\kappa)/\kappa]\Delta CF/CF_\infty \qquad (24)$$

which is an experimentally measurable quantity.

Force and Pressure

The diaphragmatic muscle force F can be determined for skeletal muscles working over joints without synergistic effects from other muscles. For the diaphragm muscle the force cannot be directly measured, rather the transdiaphragmatic pressure $P_{di}$ is obtained as a proportional measure. The following relation could be used:

$$F = \mu E \tag{25}$$

where $\mu$ is a proportionality constant and E is the signal strength of the diaphragm's electrical activity EAdi, preferably based on the first spectral moment which is rather insensitive to metabolic changes caused by fatigue. The relation to the pressure is proportional but non-linear. This fact is taken into consideration by introducing the factor G(V) which is volume (V) dependent, i.e.:

$$P_{di} = F\, G(V) \tag{26}$$

Thus, $$\mu G(V) = P_{di}/E \tag{27}$$

which also is an experimentally measurable quantity.

Myoelectric Signal Strength and Spectral Changes

Rearrangement of equation (18a) and insertion of equations (23) and (25) gives:

$$\alpha E = \beta - Q = 0 \tag{28}$$

where $$\alpha = \mu T_R/\eta \tag{29}$$

and $$\beta = F_C T_R/\eta \tag{30}$$

It can be observed that $\alpha$ is dependent, through the parameter $\mu$, on the electrode geometry and placement in relation to the muscle, while the other parameters are rather constant for similar muscles.

Experiments under fatiguing conditions at any volume give corresponding values of E and Q (through the center frequency changes). A data fitting procedure (not regression) gives numerical values to $\alpha$ and $\beta$. With $\alpha$ and $\beta$ known, an estimate of the diaphragmatic muscle force F can be obtained in relation to its fatigue threshold value, i.e.:

$$F/F_C = E\alpha/\beta \tag{31}$$

As long as $F/F_c$ is smaller than one, isometric fatigue of the patient's muscle does not develop. That means that the signal strength should be lower than the critical value:

$$E < E_{ISOM} = \beta/\alpha \tag{32}$$

For periodic muscle work, higher forces and signal levels are tolerable.

Spectral Changes as Indicators of Tolerable Concentration of Metabolites

The relative spectral change $\epsilon$ of the diaphragm's electrical activity EAdi, defined in equation (21), is an indirect measurement of remaining concentration of metabolites in the muscle during periodic fatiguing contractions. It seems that the muscle very rapidly goes into an anaerobic metabolic state once the force is higher than $F_c$ and that virtually all contractions above this level causes changes in the center frequency CFdi. Therefore it is likely that a certain small value of $\epsilon$ is tolerable as long as it is below a certain critical level, which we denote $\epsilon_C$. With this critical value introduced into equation (22) and simultaneous use of equations (18a) and (23), it can be found that a condition for long term fatigue not to occur is:

$$\kappa < 1/\{1 + [(1-\epsilon_C)/\epsilon_C] T_R (F - F_C)/\eta\} \tag{33}$$

This expression can be rearranged to give the force condition:

$$F < F_C + [(1-\kappa)/\kappa][\epsilon_C/(1-\epsilon_C)]\eta/T_R \tag{34}$$

or, together with equation (30), $$F < F_C\{1 + [(1-\kappa)/\kappa][\epsilon_C/(1-\epsilon_C)]/\beta\} \tag{35}$$

Since the force in diaphragmatic contractions cannot be simply measured, equations (33) to (35) are expressed as functions of the signal strength E and the transdiaphragmatic pressure Pdi. Use of equations (25) and (26) give for the signal strength E of the diaphragm's electrical activity EAdi:

$$\kappa < 1/\{1 + [(1-\epsilon_C)/\epsilon_C](\alpha E - \beta)\} \tag{36}$$

and $$E < \{\beta + [(1-\kappa)/\kappa][\epsilon_C/(1-\epsilon_C)]\}/\alpha \tag{37}$$

and for the transdiaphragmatic pressure Pdi:

$$\kappa < 1/\{1 + [(1-\epsilon_C)/\epsilon_C](\alpha P_{di} - \beta)\} \tag{38}$$

and $$P_{di} < \mu G(V)\{\beta + [(1-K)/K][E\,hd\,c/(1-E_c)]\}/\alpha \tag{39}$$

Non-Restrictive Illustrative Embodiment of a Method and Device for Determining an Optimal Level of Ventilatory Assist to a Ventilator Dependent Patient Non-restrictive illustrative embodiments of the method and device for determining an optimal level of ventilatory assist to a ventilator-dependent patient will now be described.

First Embodiment of FIG. 5

Operation 501

The signal strength of the diaphragm's electrical activity EAdi is monitored through a detector 502. As illustrated in FIG. 1, detector 502 may comprise, for example, a computer 4 to measure the signal strength of the electrical activity EAdi of the patient's diaphragm through a linear array 5 of electrodes mounted on an esophageal catheter 6 inserted through the patient's nostril (or patient's mouth) until the electrode array 5 is positioned in the gastro-esophageal junction 10 of the patient's diaphragm 7.

Operation 502

A calculator 503 calculates the coefficients $\alpha$ and $\beta$ using equation (28):

$$\alpha E - \beta - Q = 0 \tag{28}$$

with myoelectric data from fatigue tests (calibration). Fatigue test can be performed by either reducing the level of assist, or performing a short airway occlusion, while measuring the myoelectric activity during a few inspiratory attempts. To shorten and facilitate the fatigue test the subject could be encouraged to voluntarily increase his efforts. Such a test is routinely performed to determine the maximum inspiratory airway pressure.

Operation 504

The calculator 503 calculates the duty cycle $\kappa$ as described hereinabove.

Operation 505

The calculator 503 calculates estimates of a critical level of the relative spectral change $\kappa_C$ of the diaphragm's electrical activity EAdi from the general experimental fact that fatigue does not occur below a duty cycle of 0.2 even at maximum muscle force and that the critical force level $F_C$ is approximately 0.2 times the maximum force. Equation (33) then gives $\epsilon_C \approx \beta/(\beta+8/9)$, or, since both $\epsilon_C$ and $\beta$ are small quantities:

$$\epsilon_C \approx \beta \quad (40)$$

Operation 506

The calculator 503 calculates a critical signal strength of the diaphragm's electrical activity EAdi above which isometric muscle fatigue develops, using the relation:

$$E < E_{ISOM} = \beta/\alpha \quad (32)$$

Operation 507

If myoelectric monitoring is used (giving signal strength and duty cycle), the calculator 503 calculates a critical signal strength of the diaphragm's electrical activity EAdi above which long term muscle fatigue develops, is calculated using equation (37):

$$E < \{\beta + [1-\kappa)/\kappa][\kappa_C/(1-\epsilon_C)]\}/\alpha \quad (37)$$

Operation 508

A controller 509 controls the ventilatory assist, for example the gain of the ventilatory assist at a level such that the signal strength of the diaphragm's electrical activity EAdi does not exceed that described in relation (37) (higher support suggest unnecessary muscle inactivation) to prevent long-term muscle fatigue to develop:

$$E < \{\beta + [(1-\kappa)/\kappa][(\epsilon_C/(1-\epsilon_C)]/\alpha\} \quad (37)$$

However, the signal strength of the diaphragm's electrical activity EAdi should not exceed that described in equation (32) (this level indicates the level for muscle fatigue during isometric contractions) to prevent isometric muscle fatigue to develop:

$$E < E_{ISOM} = \beta/\alpha \quad (32)$$

Second Embodiment of FIG. 6

Operation 601

The signal strength of the diaphragm's electrical activity EAdi is monitored through a detector 602. As illustrated in FIG. 1, detector 602 may comprise, for example, a computer 4 to measure the signal strength of the electrical activity EAdi of the patient's diaphragm through a linear array 5 of electrodes mounted on an esophageal catheter 6 inserted through the patient's nostril (or patient's mouth) until the electrode array 5 is positioned in the gastro-esophageal junction 10 of the patient's diaphragm 7.

Operation 603

A detector 604 monitors the patient's transdiaphragmatic pressure $P_{di}$. As illustrated in FIG. 1, detector 604 may comprise, for example, a computer 4 to continuously measure the transdiaphragmatic pressure $P_{di}$ by detecting the esophageal $P_{es}$ and gastric $P_{ga}$ pressures through respective gastric 8 and esophageal 9 balloons mounted on the catheter 6 on opposite sides of the array 5 of electrodes, and by processing the detected esophageal $P_{es}$ and gastric $P_{ga}$ pressures to obtain the patient's transdiaphragmatic pressure $P_{di}$.

Operation 605

A calculator 606 calculates the coefficients $\alpha$ and $\beta$ using equation (28):

$$\alpha E - \beta - Q = 0 \quad (28)$$

with myoelectric data from fatigue tests (calibration). Fatigue test can be performed by either reducing the level of assist, or performing a short airway occlusion, while measuring the myoelectric activity during a few inspiratory attempts. To shorten and facilitate the fatigue test the subject could be encouraged to voluntarily increase his efforts. Such a test is routinely performed to determine the maximum inspiratory airway pressure.

Operation 607

The calculator 606 calculates the duty cycle $\kappa$ as described hereinabove.

Operation 608

The calculator 606 calculates estimates of a critical level of the relative spectral change $\epsilon_C$ of the diaphragm's electrical activity EAdi from the general experimental fact that fatigue does not occur below a duty cycle of 0.2 even at maximum muscle force and that the critical force level $F_C$ is approximately 0.2 times the maximum force. Equation (33) then gives $\epsilon_C \approx \beta/(\beta+8/9)$, or, since both $\epsilon_C$ and $\beta$ are small quantities:

$$\epsilon_C = \beta \quad (40)$$

Operation 609

The calculator 606 calculates a critical signal strength of the diaphragm's electrical activity EAdi above which isometric muscle fatigue develops, using the relation:

$$E < E_{ISOM} = \beta/\alpha \quad (32)$$

Operation 610

The calculator 606 calculates a critical level of the transdiaphragmatic pressure $P_{di}$ using relation (39):

$$P_{di} < \mu G(V) \{\beta+[(1-K)/K][E_C/(1-E_c)]\}/ \alpha tm \quad (39)$$

Operation 610 requires knowledge about the geometrical G(V) dependence. This factor G(V) can be obtained from a calibration of the experimentally measurable quantity $P_{di}/E$ as shown in equation (27):

$$\mu G(V) = P_{di}/E \quad (27)$$

Alternatively, geometrical dependence G(V) of inspiratory pressure can also be estimated by performing single or multiple breath airway occlusions at two lung volumes, e.g. end-inspiration and end expiration lung volumes, while the volume difference is measured by a computer with, for example, at least one flow meter (see computer 4 and pneumotachograph 3 of FIG. 1).

Operation 611

A controller 612 controls the ventilatory assist, for example the gain of the ventilatory assist at a level such that:
the monitored signal strength of the diaphragm's electrical activity EAdi does not exceed that described in relation (32) (this level indicates the level for muscle fatigue during isometric contractions) to prevent isometric muscle fatigue to develop:

$$E < E_{ISOM} = \beta/\alpha \quad (32)$$

the monitored patient's transdiaphragmatic pressure $P_{di}$ does not exceed that described in relation (39) to prevent long-term muscle fatigue to develop:

$$P_{di} < \mu G(V) \{\beta+[(1-\kappa)][\epsilon_C/(1-\epsilon_C)]\} \quad (39)$$

Although the present invention has been described hereinabove with reference to non-restrictive illustrative embodiments thereof, it should be kept in mind that these embodiments can be modified at will within the scope of the appended claims without departing from the spirit and nature of the present invention. In particular but not exclusively:
the present invention pertains not only to CFdi and RMS but possibly to other types of measures;
the present invention can be implemented through measurement of the electrical activity of respiration-related muscles other than the diaphragm; and the present invention is concerned with any method of mechanical ventilation, including negative pressure ventilation.

References

[1] Aldrich T K, Sinderby C, McKenzie D K, Estenne M, and Gandevia S C. Electrophysiologic Techniques for the Assessment of Respiratory Muscle Function. In ATS/ERS Statement on respiratory muscle testing. Am J Respir Crit Care Med 166: 610-623, 2002.

[2] Bellemare F, and Grassino A. Effect of pressure and timing of contraction on human diaphragm fatigue. J Appl Physiol: Respirat Environ Exercise Physiol 53: 1190-1195, 1982.

[3] Bellemare F, and Grassino A. Evaluation of human diaphragm fatigue. J Appl Physiol Respirat Environ Exercise Physiol 53: 1196-1206, 1982.

[4] Beck J, Sinderby C, Lindström L, and Grassino A. Influence of bipolar electrode positioning on measurements of human crural diaphragm EMG. J Appl Physiol 81: 1434-1449, 1996.

[5] Beck J, Sinderby C, Lindström L, and Grassino A. Diaphragm interference pattern EMG and compound muscle action potentials: effects of chest wall configuration. J. Appl. Physiol. 82: 520-530, 1997.

[6] Beck J, Sinderby C, Lindström L, and Grassino A. Effects of lung volume on diaphragm EMG signal strength during voluntary contractions. J Appl Physiol 85: 1123-1134, 1998.

[7] Beck J, Sinderby C, Weinberg J, and Grassino A. Effects of muscle-to-electrode distance on the human diaphragm electromyogram. J Appl Physiol 79: 975-985, 1995.

[8] Brochard L, Harf A, Lorino H, and Lemaire F. Inspiratory pressure support prevents diaphragmatic fatigue during weaning from mechanical ventilation. Am Rev Respir Dis 139: 513-521, 1989.

[9] Broman, H. An investigation on the influence of a sustained contraction on the succession of action potentials from a single motor unit. Electromyogr Clin Neurophysiol 17:341-58, 1977.

[10] Calzia E, Lindner K H, Witt S, Schirmer U, Lange H, Stenz R, and Georgieff M. Pressure-time product and work of breathing during biphasic continuous positive airway pressure and assisted spontaneous breathing. Am J Respir Crit Care Med 150: 904-910, 1994.

[11] Clanton T L, Hartman E, and Julian M W. Preservation of sustainable inspiratory muscle pressure at increased end-expiratory lung volume. Am Rev Respir Dis 147: 385-391, 1993.

[12] Clausen T, and Everts M E. K+ induced inhibition of contractile force in rat skeletal muscle, role of Na+-K+ transport. Am J Physiol 261 (Cell Physiol. 30): C799-C807, 1991.

[13] Cohen C A, Zagelbaum G, Gross D, Roussos C, and Macklem P T. Clinical manifestations of respiratory muscle fatigue. Am J Med 73: 308-316, 1982.

[14] Farkas G A and Roussos C H. Acute diaphragmatic shortening: In vitro mechanics and fatigue. Am Rev Respir Dis 130: 434-438, 1984.

[15] Gandevia S C, and McKenzie D K. Human diaphragmatic EMG: changes with lung volume and posture during supramaximal phrenic nerve stimulation. J Appl Physiol 60: 1420-1428, 1986.

[16] Gross D, Grassino A, Ross W R D, and Macklem P T. Electromyogram pattern of diaphragmatic fatigue. J Appl Physiol: Respirat Environ Exercise Physiol 46: 1-7, 1979.

[17] Hodgkin A L. A note on conduction velocity. J Physiol (Lond) 125: 221-224, 1954.

[18] Hodgkin A L and Huxley A F. A quantitative description of membrane current and its application to conduction and excitation in nerve. J Physiol (Lond) 117: 500-544, 1952.

[19] Hussain S. Regulation of ventilatory muscle blood flow. J Appl Physiol 81: 1455-1468, 1996.

[20] Jubran A, Van de Graaff W B, and Tobin M J. Variability of patient-ventilator interaction with pressure support ventilation in patients with chronic obstructive pulmonary disease. Am J Respir Crit Care Med 152: 129-136, 1995.

[21] Kadefors R, Kaiser E, and Petersen I. Dynamic spectrum analysis of myo-potential with special reference to muscle fatigue. Electromyog Clin Neurophysiol 8: 39-74, 1968.

[22] Klawitter P F, and Clanton T L. Tension-time index, fatigue, and energetics in isolated rat diaphragm: a new experimental model. J Appl Physiol 96: 89-95, 2003.

[23] Körner L, Parker P, Almstrom C, Herberts P, and Kadefors R. The relation between spectral changes of the myoelectric signal and the intramuscular pressure of the human skeletal muscle. Eur J Appl Physiol 52: 202-206, 1984.

[24] Laghi F, Caffapan S E, Jubran A, Parthasarathy S, Warshawsky P, Choi Y-S A, and Tobin M J. Is weaning failure caused by low-frequency fatigue of the diaphragm? Am J Respir Crit Care Med 167: 120-127, 2003.

[25] Lindinger M I, and Sjo gaard G. Potassium regulation during exercise and recovery. Sports Med 11:382-401, 1991.

[26] Lindstrom, L. Fatigue changes in the myoelectric signal during periodic muscle work. Bull Eur Physiopathol Respir 15 Suppl: 107-114, 1979.

[27] Lindstrom, L and Hellsing, G. Masseter muscle fatigue in man objectively quantified by analysis of myoelectric signals. Arch Oral Biol 28:297-301, 1983.

[28] Lindström L, Kadefors R, and Petersén I. An electromyographic index for localized muscle fatigue. J Appl Physiol: Respirat Environ Exercise Physiol 43: 750-754, 1977.

[29] Lindström L and Magnusson R. Interpretation of myoelectric power density spectra: a model and its application. Proc IEEE 65: 653-662, 1977.

[30] Lindström L, and Petersen I. Power spectrum analysis of EMG signals and its applications. In: Progress in Clinical Neurophysiology. Computer-Aided Electromyography, edited by Desmedt J E. Basel: Karger, vol. 10, 1983 p. 1-51.

[31] Mortimer J T, Magnusson R, and Petersen I. Conduction velocity in ischemic muscle: effect on EMG frequency spectrum. Am J Physiol 219: 1324-1329, 1970.

[32] Ranieri V M, Giuliani R, Mascia L, Grasso S, Petruzzelli V, Puntillo N, Perchiazzi G, Fiore T, and Brienza A. Patient-ventilator interaction during acute hypercapnia: pressure-support vs. proportional-assist ventilation. J Appl Physiol 81:426-36, 1996.

[33] Roussos C, Fixley M, Gross D, and Macklem P T. Fatigue of inspiratory muscles and their synergistic behavior. J Appl Physiol: Respirat Environ Exercise Physiol 46: 897-905, 1979.

[34] Roussos C S and Macklem P T. Diaphragmatic fatigue in man. J Appl Physiol:Respirat Environ Exercise Physiol 43: 189-197, 1977.

[35] Sasson C S H, Light R W, Lodio R, Siek G C, and Mahutte C K. Pressure-time product during continuous positive airway pressure, pressure support ventilation, and T-piece during weaning from mechanical ventilation Am Rev Respir Dis 143: 469-475, 1991.

[36] Sinderby C, Beck J C, Lindström L, and Grassino A. Enhancement of signal quality in esophageal recordings of diaphragm EMG. J Appl Physiol 82: 1370-1377, 1997.

[37] Sinderby C, Beck J, Weinberg J, Spahija J, and Grassino A. Voluntary activation of the human diaphragm in health and disease. J Appl Physiol 85: 2146-2158, 1998.

[38] Sinderby C A, Comtois A S, Thomson R G, and Grassino A E. Influence of the bipolar electrode transfer function on the electromyogram power spectrum. Muscle & Nerve 19: 290-301, 1996.

[39] Sinderby C, Lindstrom L, Comtois N, and Grassino A E. Effects of diaphragm shortening on the mean action potential conduction velocity in canines. J Physiol 490: 207-214, 1996.

[40] Sinderby C, Lindström L, and Grassino A. Automatic assessment of electromyogram quality. J Appl Physiol 79: 1803-1815, 1995.

[41] Sinderby C, Navalesi P, Beck J, Skrobik Y, Comtois N, Friberg S, Gottfried S B, and Lindstrom L. Neural control of mechanical ventilation. Nat Med 5: 1433-1436, 1999.

[42] Sinderby C, Spahija J, and Beck J. Changes in respiratory effort sensation over time are linked to the frequency content of diaphragm electrical activity. Am J Respir Crit Care Med 163: 905-910, 2001.

[43] Tobin M J, Perez W, Guenther S M, Semmes B J, Mador M J, Allen S J, Lodato R F, Dantzker D R. The pattern of breathing during successful and unsuccessful trials of weaning from mechanical ventilation. Am Rev Respir Dis 134:1111-1118, 1986.

[44] Tzelepis G, McCool F D, Leith D E, and Hoppin F G Jr. Increased lung volume limits endurance of inspiratory muscles. J Appl Physiol 64: 1796-1802, 1988.

What is claimed is:

1. A method for determining a level of ventilatory assist to a ventilator-dependent patient for reducing the risk of respiratory muscle fatigue, comprising:
   detecting a respiration-related feature of the ventilator-dependent patient and producing a signal representative of the detected respiration-related feature;
   calculating a critical threshold of the respiration-related feature, wherein fatigue of a respiratory muscle of the ventilator-dependent patient develops when the signal representative of the detected respiration-related feature exceeds the critical threshold; and
   controlling the level of ventilatory assist to the ventilator-dependent patient to prevent the signal representative of the detected respiration-related feature exceeding the critical threshold and thereby prevent fatigue of the respiratory muscle to develop.

2. A method for determining a level of ventilatory assist as defined in claim 1, wherein:
   detecting the respiration-related feature comprises detecting a signal strength of an electrical activity of the respiratory muscle;
   calculating the critical threshold comprises calculating a critical signal strength of the electrical activity of the respiratory muscle, wherein fatigue of the respiratory muscle develops when the detected signal strength of the electrical activity of the respiratory muscle exceeds the calculated critical signal strength; and
   controlling the level of ventilatory assist comprises preventing the detected signal strength of the electrical activity of the respiratory muscle to exceed the calculated critical signal strength to prevent fatigue of the respiratory muscle.

3. A method for determining a level of ventilatory assist as defined in claim 2, wherein calculating the critical signal strength of the electrical activity of the respiratory muscle comprises:
   calculating a critical value of a relative spectral change of the electrical activity of the respiratory muscle above which long term fatigue of the respiratory muscle develops; and
   using the critical value of the relative spectral change to calculate the critical signal strength of the electrical activity of the respiratory muscle.

4. A method for determining a level of ventilatory assist as defined in claim 2, wherein calculating the critical signal strength of the electrical activity of the respiratory muscle comprises:
   determining a critical respiratory muscle force level above which muscle fatigue starts to develop; and
   in response to the critical respiratory muscle force level, calculating the critical signal strength of the electrical activity of the respiratory muscle under which isometric fatigue of the respiratory muscle does not develop.

5. A method for determining a level of ventilatory assist as defined in claim 1, wherein:
   detecting the respiration-related feature comprises detecting a transdiaphragmatic pressure of the ventilator-dependent patient;
   calculating the critical threshold of the respiration-related feature comprises calculating a critical level of the transdiaphragmatic pressure of the ventilator-dependent patient above which muscle fatigue develops; and
   controlling the level of ventilatory assist comprises preventing the detected transdiaphragmatic pressure to exceed the calculated critical level of the transdiaphragmatic pressure to prevent fatigue of the respiratory muscle.

6. A method for determining a level of ventilatory assist as defined in claim 5, wherein calculating the critical level of the transdiaphragmatic pressure comprises:
   calculating a critical value of a relative spectral change of an electrical activity of the respiratory muscle above which long term fatigue of the respiratory muscle develops;
   calculating a respiratory duty cycle; and
   using the critical value of the relative spectral change and the respiratory duty cycle to calculate the critical level of the transdiaphragmatic pressure.

7. A method for determining a level of ventilatory assist as defined in claim 1, wherein calculating the critical threshold of the respiration-related feature comprises:
   detecting a signal strength of an electrical activity of the respiratory muscle;
   calculating a first critical signal strength of the electrical activity of the respiratory muscle above which muscle fatigue develops; and
   determining a critical muscle force level above which muscle fatigue develops and, in response to the critical muscle force level, calculating a second critical signal strength of the electrical activity of the respiratory muscle under which isometric fatigue of the respiratory muscle does not develop;
   wherein controlling the level of ventilatory assist comprises preventing the detected signal strength of the electrical activity of the respiratory muscle to exceed either the first and second critical signal strengths to prevent fatigue of the respiratory muscle.

8. A method for determining a level of ventilatory assist as defined in claim 1, wherein:
   detecting the respiration-related feature comprises:
   detecting a transdiaphragmatic pressure of the ventilator-dependent patient; and detecting a signal strength of an electrical activity of the respiratory muscle;

calculating the critical threshold of the respiration-related feature comprises:

calculating a critical level of the transdiaphragmatic pressure above which muscle fatigue develops; and calculating a critical signal strength of an the electrical activity of the respiratory muscle above which muscle fatigue develops; and controlling the level of ventilatory assist comprises:

preventing the detected transdiaphragmatic pressure to exceed the critical level of the transdiaphragmatic pressure to prevent fatigue of the respiratory muscle; and preventing the detected signal strength of the electrical activity of the respiratory muscle to exceed the critical signal strength to prevent fatigue of the respiratory muscle.

9. A method for determining a level of ventilatory assist as defined in claim 1, wherein the respiratory muscle of the ventilator-dependent patient comprises the patient's diaphragm.

10. A device for determining a level of ventilatory assist to a ventilator-dependent patient for reducing the risk of respiratory muscle fatigue, comprising:

a detector of a respiration-related feature of the ventilator-dependent patient to produce a signal representative of the detected respiration-related feature;

a calculator of a critical threshold of the respiration-related feature, wherein fatigue of a respiratory muscle of the ventilator-dependent patient develops when the signal representative of the detected respiration-related feature exceeds the critical threshold; and a controller of the level of ventilatory assist to the ventilator-dependent patient to prevent the signal representative of the detected respiration-related feature to exceed the calculated critical threshold of the respiration-related feature and thereby prevent fatigue of the respiratory muscle to develop.

11. A device for determining a level of ventilatory assist as defined in claim 10, wherein:

the detector detects a signal strength of an electrical activity of the respiratory muscle;

the calculator calculates a critical signal strength of the electrical activity of the respiratory muscle, wherein fatigue of the respiratory muscle develops when the detected signal strength of the electrical activity of the respiratory muscle exceeds the calculated critical signal strength; and the controller prevents the detected signal strength of the electrical activity of the respiratory muscle to exceed the calculated critical signal strength to prevent fatigue of the respiratory muscle.

12. A device for determining a level of ventilatory assist as defined in claim 11, wherein the calculator:

calculates a critical value of a relative spectral change of the electrical activity of the respiratory muscle above which long term fatigue of the respiratory muscle develops; and uses the critical value of the relative spectral change to calculate the critical signal strength of the electrical activity of the respiratory muscle.

13. A device for determining a level of ventilatory assist as defined in claim 11, wherein the calculator:

determines a critical respiratory muscle force level above which muscle fatigue starts to develop; and in response to the critical respiratory muscle force level, calculates the critical signal strength of the electrical activity of the respiratory muscle under which isometric fatigue of the respiratory muscle does not develop.

14. A device for determining a level of ventilatory assist as defined in claim 10, wherein:

the detector detects a transdiaphragmatic pressure of the ventilator-dependent patient;

the calculator computes a critical level of the transdiaphragmatic pressure of the ventilator-dependent patient above which muscle fatigue develops; and the controller prevents the detected transdiaphragmatic pressure to exceed the critical level of the transdiaphragmatic pressure to prevent fatigue of the respiratory muscle.

15. A device for determining a level of ventilatory assist as defined in claim 14, wherein the calculator:

calculates a critical value of a relative spectral change of an electrical activity of the respiratory muscle above which long term fatigue of the respiratory muscle develops;

calculates a respiratory duty cycle; and uses the critical value of the relative spectral change and the respiratory duty cycle to calculate the critical level of the transdiaphragmatic pressure.

16. A device for determining a level of ventilatory assist as defined in claim 10, wherein:

the detector detects a signal strength of an electrical activity of the respiratory muscle;

the calculator (a) calculates a first critical signal strength of an the electrical activity of the respiratory muscle above which muscle fatigue develops, and (b) determines a critical muscle force level above which muscle fatigue starts to develop and, in response to the critical muscle force level, calculates a second critical signal strength of the electrical activity of the respiratory muscle under which isometric fatigue of the respiratory muscle does not develop; and the controller prevents the detected signal strength of the electrical activity of the respiratory muscle to exceed either the first and second critical signal strengths to prevent fatigue of the respiratory muscle.

17. A device for determining a level of ventilatory assist as defined in claim 10, wherein:

the detector comprises a first detector of a transdiaphragmatic pressure of the ventilator-dependent patient, and a second detector of a signal strength of an electrical activity of the respiratory muscle;

the calculator (a) calculates a critical level of the transdiaphragmatic pressure above which muscle fatigue develops, and (b) calculates a critical signal strength of the electrical activity of the respiratory muscle above which muscle fatigue develops; and the controller (a) prevents the detected transdiaphragmatic pressure to exceed the critical level of the transdiaphragmatic pressure to prevent fatigue of the respiratory muscle, and (b) prevents the detected signal strength of the electrical activity of the respiratory muscle to exceed the critical signal strength to prevent fatigue of the respiratory muscle.

18. A device for determining a level of ventilatory assist as defined in claim 10, wherein the respiratory muscle of the ventilator-dependent patient comprises the patient's diaphragm.

* * * * *

UNITED STATES PATENT AND TRADEMARK OFFICE
CERTIFICATE OF CORRECTION

| | | |
|---|---|---|
| PATENT NO. | : 8,256,419 B2 | Page 1 of 1 |
| APPLICATION NO. | : 10/589385 | |
| DATED | : September 4, 2012 | |
| INVENTOR(S) | : Christer Sinderby et al. | |

It is certified that error appears in the above-identified patent and that said Letters Patent is hereby corrected as shown below:

In the claims:

In column 23, claim 8, line 7, delete "an".

Signed and Sealed this
Twentieth Day of November, 2012

David J. Kappos
*Director of the United States Patent and Trademark Office*